(12) United States Patent
Boyle, Jr. et al.

(10) Patent No.: US 10,881,484 B2
(45) Date of Patent: Jan. 5, 2021

(54) MEDICAL TUBE CLEARANCE DEVICE

(71) Applicant: ClearFlow, Inc., Irvine, CA (US)

(72) Inventors: Edward M. Boyle, Jr., Bend, OR (US); Kenneth J. Chesnin, Long Beach, CA (US); Wayne A. Noda, Mission Viejo, CA (US); Paul Molloy, Irvine, CA (US); Al Diaz, Irvine, CA (US); Daniel Hyman, Foothill Ranch, CA (US); Jon D. Jacobson, Irvine, CA (US)

(73) Assignee: CLEARFLOW, INC., Irvine, CA (US)

( * ) Notice: Subject to any disclaimer, the term of this patent is extended or adjusted under 35 U.S.C. 154(b) by 0 days.

(21) Appl. No.: 16/740,988

(22) Filed: Jan. 13, 2020

(65) Prior Publication Data

US 2020/0222148 A1 Jul. 16, 2020

Related U.S. Application Data

(60) Provisional application No. 62/791,322, filed on Jan. 11, 2019.

(51) Int. Cl.
| | |
|---|---|
| *A61B 90/70* | (2016.01) |
| *A61M 16/00* | (2006.01) |
| *A61M 27/00* | (2006.01) |
| *A61M 25/00* | (2006.01) |

(52) U.S. Cl.
CPC ............ *A61B 90/70* (2016.02); *A61M 16/00* (2013.01); *A61M 27/00* (2013.01); *A61B 2090/701* (2016.02); *A61M 2025/0019* (2013.01); *A61M 2209/10* (2013.01)

(58) Field of Classification Search
CPC ............ A61B 90/70; A61B 2034/301; A61M 25/09041; A61M 25/0113
USPC .......................................................... 604/267
See application file for complete search history.

(56) References Cited

U.S. PATENT DOCUMENTS

| 5,738,213 A | * | 4/1998 | Whiting .............. A61M 25/002 |
| | | | 206/210 |
| 7,951,243 B2 | | 5/2011 | Boyle, Jr. et al. |
| 10,265,442 B2 | | 4/2019 | Luxon et al. |
| 2012/0071822 A1 | * | 3/2012 | Romo ..................... A61B 8/12 |
| | | | 604/95.04 |
| 2014/0276948 A1 | * | 9/2014 | Zirps ...................... A61B 34/30 |
| | | | 606/130 |
| 2015/0231313 A1 | * | 8/2015 | O'Keefe ............. A61M 1/0078 |
| | | | 604/500 |
| 2015/0231361 A1 | | 8/2015 | Okeefe et al. |
| 2017/0143880 A1 | | 5/2017 | Luxon et al. |
| 2018/0036158 A1 | * | 2/2018 | Nakaya ............... A61M 25/104 |
| 2018/0104405 A1 | * | 4/2018 | Orwig ................ A61M 1/0086 |
| 2019/0201596 A1 | | 7/2019 | Luxon et al. |

* cited by examiner

*Primary Examiner* — Brandy S Lee
*Assistant Examiner* — Nidah M Hussain
(74) *Attorney, Agent, or Firm* — Pearne & Gordon LLP

(57) ABSTRACT

A device for clearing obstructions from a medical tube includes a housing defining an interior, an exterior, and a port providing fluid communication therebetween. The device further includes an elongated guide wire residing at least partially within the housing, and first and second rollers defining a nip therebetween that are located within the housing. A guide wire extends through the nip and is drivable for advancement and retraction thereof through the port via rotation of the rollers.

27 Claims, 14 Drawing Sheets

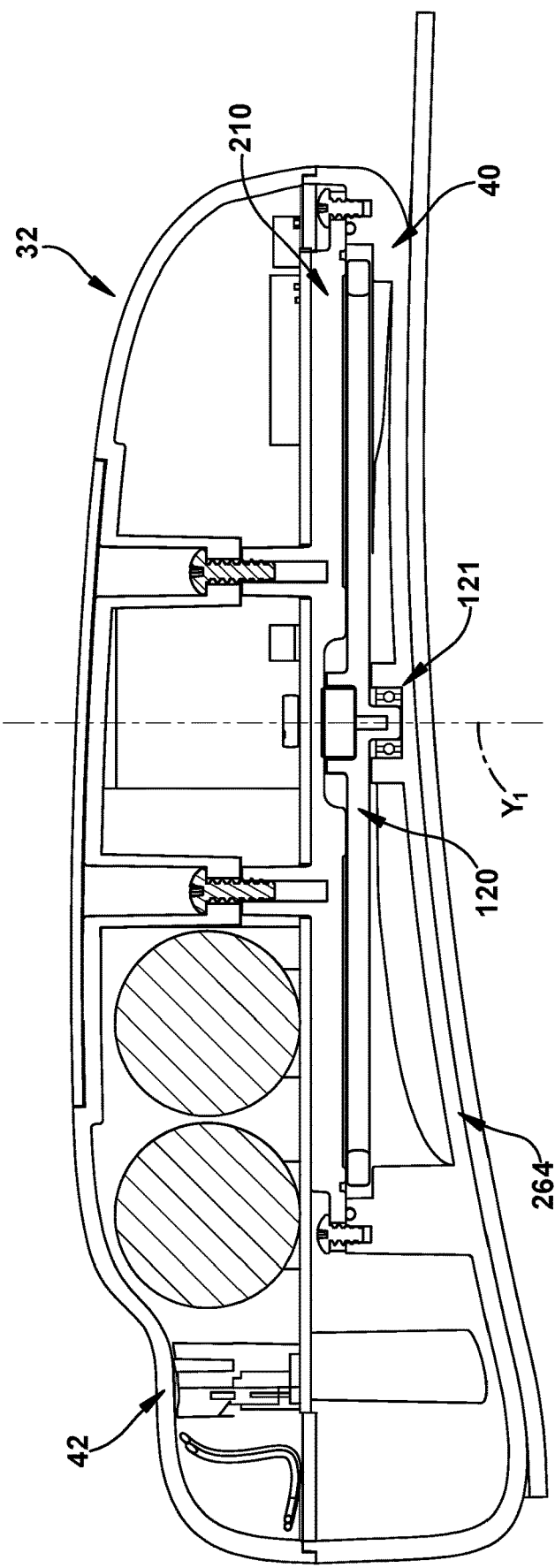

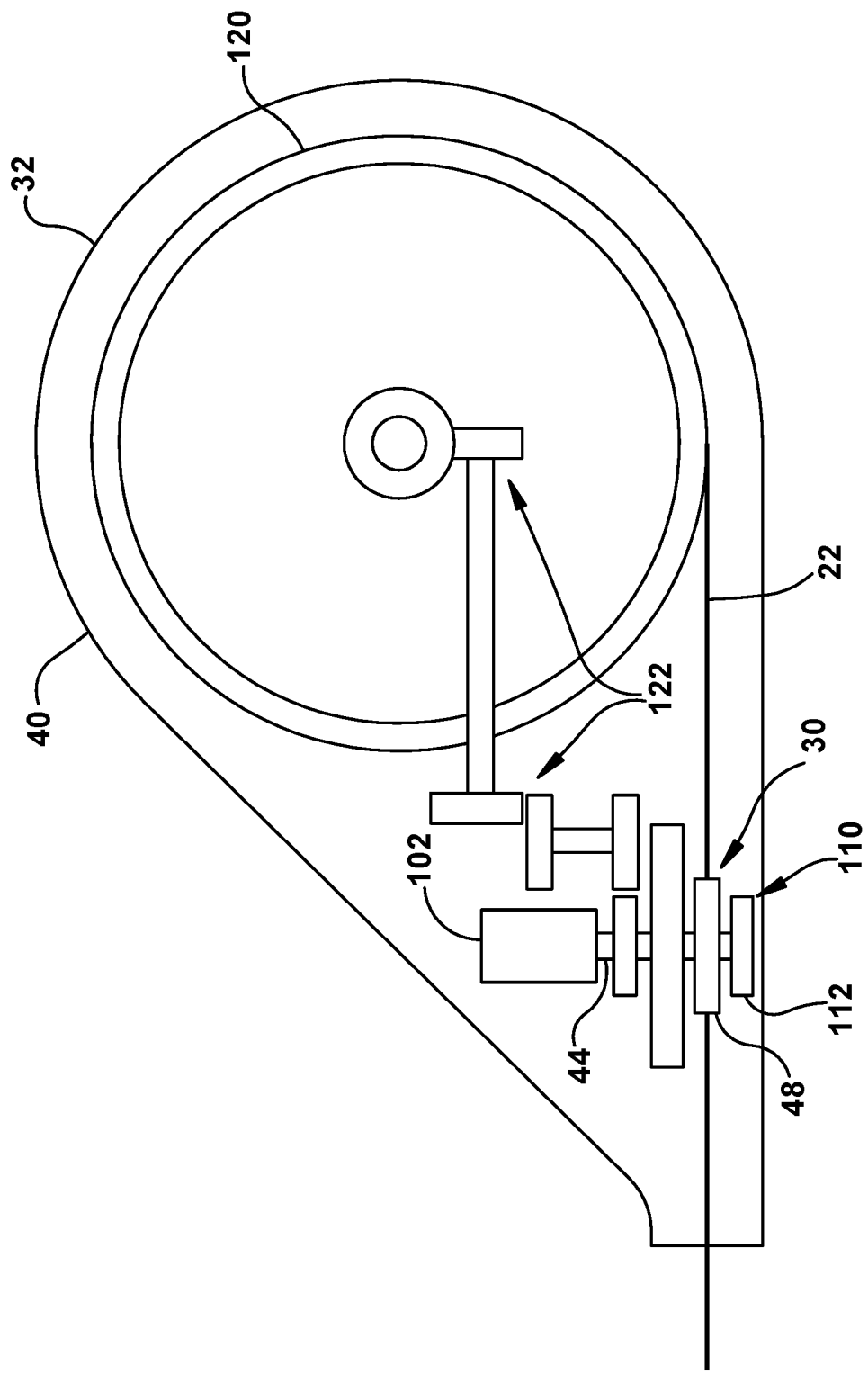

MEDICAL TUBE CLEARANCE DEVICE

CROSS REFERENCE TO RELATED APPLICATIONS

This application claims priority to U.S. Provisional Patent Application Ser. No. 62/791,322 filed Jan. 11, 2019, the contents of which are incorporated herein by reference.

TECHNICAL FIELD

This application relates generally to a medical tube assembly and, more specifically, to a device for clearing obstructions from a medical tube of the medical tube assembly.

BACKGROUND

Medical tubes can be used to deliver fluids or devices into a patient's body and/or to drain bodily fluids and secretions from compartments and structures within the body. For example, medical tubes can be used to drain fluid from one's bladder, from the colon or other portions of the alimentary tract, or from the lungs or other organs in conjunction with various therapies. As another example, medical tubes can be used to drain blood and other fluids that typically accumulate within the body cavity following traumatic surgery. As yet another example, medical tubes can be used to deliver fluids to a patient's body for nourishment or they can be used to provide access to the vasculature for removal or delivery of fluids or devices. Typically, a medical tube is inserted into the patient so that its distal end is provided in or adjacent the space where it is desired to remove or deliver material while a proximal portion remains outside the patient's body, where it can be connected, for example, to a suction source.

Fluids passing through a medical tube (particularly those including blood or blood platelets) can form clots or other obstructions within the medical tube, which can partially or totally obstruct the suction pathway within the tube. Obstruction of the medical tube can impact its effectiveness to remove or deliver the fluid and other material for which it was originally placed, eventually rendering the medical tube partially or totally non-functional. In some cases, a non-functional tube can have serious or potentially life-threatening consequences. For example, if there is a blockage in a chest tube following cardiac or pulmonary surgery, the resulting accumulation of fluid around the heart and lungs without adequate drainage can cause serious adverse events such as pericardial tamponade and pneumothorax.

SUMMARY

The following presents a simplified summary of the disclosure in order to provide a basic understanding of some example aspects described in the detailed description.

In accordance with a first aspect, a device for clearing obstructions from a medical tube includes a housing defining an interior, an exterior, and a port providing communication therebetween. The device further includes an elongated guide wire residing at least partially within the housing, and first and second rollers defining a nip therebetween. The guide wire is adapted to extend through the nip and be drivable for advancement and retraction thereof through the port via rotation of the rollers.

Optionally, the device includes a first roller shaft coupled to the first roller and being rotatable therewith about a first roller axis, a second roller shaft coupled to the second roller axis, and being rotatable therewith about a second roller axis, and a transmission operatively connected to each of the first and second roller shafts and configured to synchronize rotation thereof about their associated roller axes in opposing directions. Optionally, the transmission includes a first gear fixed to the first roller shaft and a second gear fixed to the second roller shaft.

Optionally, the device includes a wall that defines a roller shaft opening, the first roller shaft extending through the roller shaft opening. The device optionally further includes a seal member provided about the first roller shaft that inhibits fluid communication through the roller shaft opening.

Optionally, the second roller is rotatably supported by a movable carriage configured to move between a disengaged position where the second roller does not interact with the first roller and an engaged position where the second roller interacts with the first roller to thereby define the nip therebetween.

Optionally, the carriage is pivotable about a carriage axis that is spaced from and substantially parallel to the second roller axis in order to move the carriage between the disengaged and engaged positions.

Optionally, the device includes an actuator that is accessible from the exterior to move the actuator from a first position to a second position, the actuator being configured to move the carriage from the disengaged position to the engaged position as the actuator is moved from the first position to the second position.

Optionally, the actuator includes a cam body with a cam surface that engages the carriage as the actuator is moved from the first position to the second position to move the carriage from the disengaged position to the engaged position.

Optionally, the device includes a guide passage having an inner surface, the actuator being slidably received through the guide passage. Moreover, the device optionally includes a seal member configured to establish a seal between the actuator and the inner surface of the guide passage.

Optionally, when the actuator is in the first position, the interior and exterior of the housing are in fluid communication through the guide passage. Moreover, when the actuator is in the second portion, the seal inhibits fluid communication through the guide passage.

Optionally, the device further includes a power circuit for supplying electrical energy to a motor for rotating at least one of the first and second rollers. The carriage is configured to open the power circuit when the carriage is in the disengaged position and to close the circuit when the carriage is in the engaged position.

Optionally, the device includes a spool within the housing for dispensing and accumulating the elongated guide wire, the spool being rotatable relative to the housing about a spool axis.

Optionally, the elongated guide wire is coupled to the spool, and the spool is configured to freely rotate relative to the housing such that the spool passively rotates in response to compressive and tensile forces in the elongated guide wire as the elongated guide wire is driven through the nip.

Optionally, the device further includes a guide wall that extends at least partially about the circumference of the spool, the guide wall having an axis of curvature that is coaxial with the spool axis.

Optionally, the guide wall includes a rim and a plurality of guide projections that extend radially inward from the rim toward the spool and are circumferentially spaced about the spool.

Optionally, the device further includes a magnet coupled to the spool, and an encoder configured to detect a rotary position of the magnet about the spool axis.

Optionally, an outer surface portion of the housing is concave in order to accommodate a curvature of a patient's body to which the device is to be mounted in use.

Optionally, the device further includes a flexible substrate adhered and conforming to the concave outer surface portion and having an exposed surface with an adhesive for adhering the device to a patient's body in use.

Optionally, the device further includes a motor within the housing operable to drive at least one of the first roller and the second roller in order to drive the guide wire through the nip; a power supply within the housing coupled to the motor via a power circuit to supply electrical energy thereto; a user interface on the housing accessible from the exterior; and a controller within the housing operatively coupled to the motor and to the user interface, and configured to receive user inputs from the user interface for directing the advancement or withdrawal of the guide wire, and to control operation of the motor for driving the guide wire based on the user inputs. Optionally, the device is a self-contained, portable unit.

Optionally, the first and second rollers are located within the housing.

Optionally, a medical tube assembly includes the device, the medical tube, and a connector for connecting the device to the medical tube. Moreover, the connector includes a body that defines a distal branch, a proximal branch, and a drain branch, all of which being in fluid communication with one another via a common hub chamber. The proximal branch is rotatably coupled to the port in order to accommodate the guide wire therethrough.

Optionally, the connector includes one or more guide bodies within the proximal branch, each guide body being tubular in shape, with an outer diameter that approximates an inner diameter of the proximal branch, and a through-hole that extends through the guide body.

Optionally, the body of the connector defines an access branch in fluid communication with the hub chamber, and the connector further includes a valve assembly that is operable to provide selective communication through the access branch.

Optionally, a device for clearing obstructions from a medical tube includes a housing defining an interior, an exterior, and a port providing fluid communication therebetween. The device further includes an elongated guide wire residing at least partially within the housing. An outer surface portion of the housing is concave in order to accommodate a curvature of a patient's body to which the device is to be mounted in use. The guide wire is adapted to be drivable for advancement and retraction through the port and into a medical tube.

BRIEF DESCRIPTION OF THE DRAWINGS

FIG. 5A is an enlarged view of a cam body of the clearance device;

FIG. 7A is a cross-section view showing a bearing for the spool of the clearance device;

FIG. 8 is a schematic view of an example transmission that operatively couples a motor of the clearance device with the spool;

DETAILED DESCRIPTION

Figure 1:
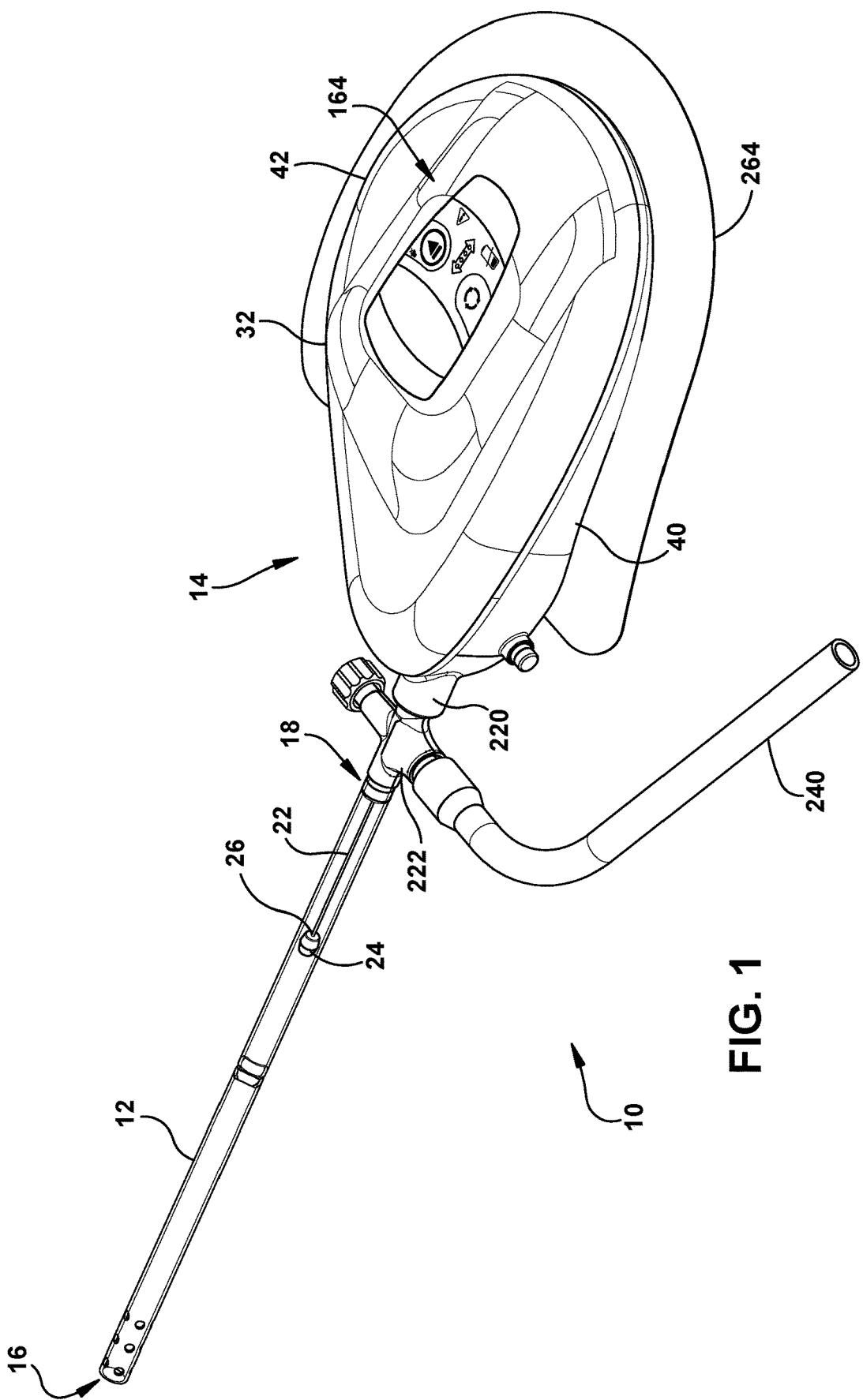
FIG. 1 is a perspective view of an example medical tube assembly.

Certain terminology is used herein for convenience only and is not to be taken as a limitation on the present invention. Relative language used herein is best understood with reference to the drawings, in which like numerals are used to identify like or similar items. Further, in the drawings, certain features may be shown in schematic form.

It is to be noted that the terms "proximal" and "distal" as used herein when describing two ends or portions of a feature indicate a relative positioning that those two ends or portions will generally have along an in-line system relative to a patient, the distal end or portion being closer to (or more advanced within) the patient than the proximal end or portion. For example, in an in-line system comprising a tube that draws fluid from the patient through the tube along a flow path, a distal end or portion of the tube will be closer to (likely implanted within) a patient than a proximal end or portion, which will be outside the patient) along the flow path of the fluid.

It is further to be noted that the term "coupled" as used herein when describing two or more features means that the features can be integral with each other or that the features can be separate features that are removably or non-removably attached to each other using various means such as threads, fasteners, hooks, clips, adhesive, welds, or other means of attaching two separate features. The features may be movably coupled to each other such that each feature is movable (e.g., slidable, rotatable, etc.) relative to the other, or the features may be fixedly coupled to each other such that neither feature can substantially move relative to the other.

Examples will now be described more fully hereinafter with reference to the accompanying drawings in which example embodiments are shown. Whenever possible, the same reference numerals are used throughout the drawings to refer to the same or like parts. However, aspects may be embodied in many different forms and should not be construed as limited to the embodiments set forth herein.

As shown in FIG. 1, an example medical tube assembly 10 includes a medical tube 12 and a device 14 for clearing obstructions from the medical tube 12. The medical tube 12 is a tube having a length, an inner diameter, and an outer diameter that can each vary between different embodiments. Indeed, the medical tube 12 can have a variety of different shapes and configurations. The medical tube 12 can be used to drain bodily fluids and secretions from within body compartments and structures such as, for example, fluid from within a person's bladder, colon, lungs, brain, thoracic cavity, or any other body structure. The medical tube 12 can alternatively be used to deliver fluids, solids, semi-solids, or devices to a body compartment or structure. In some examples, the medical tube 12 can be used to both drain bodily fluids and deliver fluids.

The medical tube 12 has a distal opening 16 and a proximal opening 18 and can be inserted into a patient so that its distal opening 16 is provided in or adjacent the space where it is desired to remove or deliver material, while the proximal opening 18 remains outside the patient's body. In the example shown in FIG. 1, the proximal opening 18 and distal opening 16 respectively coincide with proximal and distal ends of the medical tube 12.

The clearance device 14 includes a guide wire 22 that can be advanced or withdrawn through the medical tube 12 to help dislodge or draw obstructing material within the medical tube 12. Moreover, one or more clearance members 24 can be coupled to a distal end 26 or other portions of the guide wire 22 to aid in dislodging or drawing of material as the guide wire 22 translates through the medical tube 12. In the illustrated embodiment, the guide wire 22 is circular in cross-section and is made of a material with elastic or shape memory properties such as, for example, nickel-titanium. Moreover, a single clearance member 24 in the form of a bead is coupled to the distal end 26 of the guide wire 22. However, the guide wire 22 may include or be made of other shapes or materials, and one or more clearance members 24 of other forms may be coupled to the guide wire 22 in other embodiments. Various examples of possible guide wires and clearance members are disclosed in U.S. Pat. No. 7,951,243 and U.S. Pat. App. Pub. Nos. 2015/0231313 and 2015/0231361, which are incorporated by reference herein in their entirety.

Figure 2:
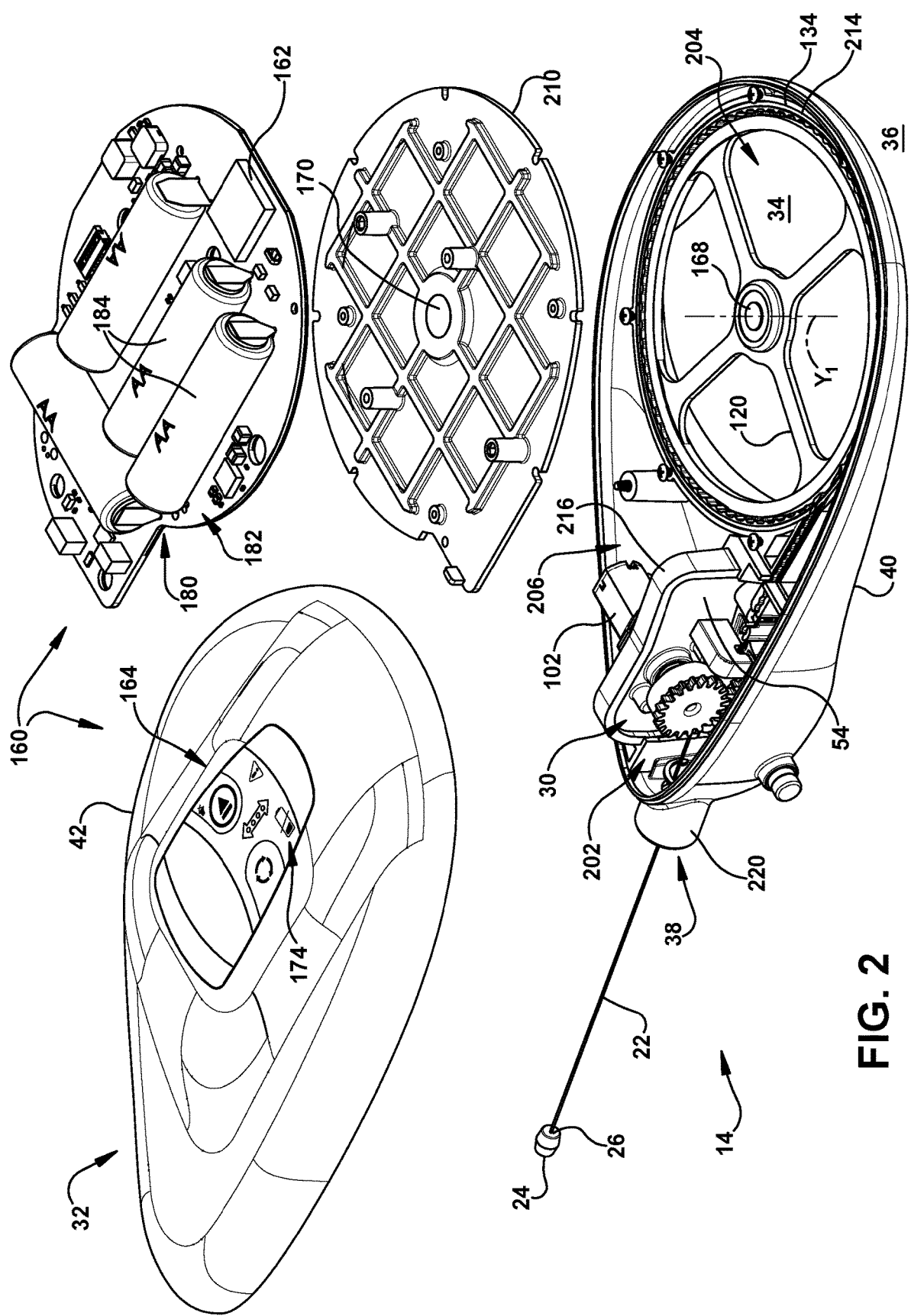
FIG. 2 is an exploded view of a clearance device for the medical tube assembly with a housing portion removed.

Turning to FIG. 2, the clearance device 14 further includes a roller assembly 30 that, as discussed further below, is operable to advance or retract the guide wire 22 through the medical tube 12. Moreover, the clearance device 14 includes a housing 32 configured to preserve a sterile field within the housing 32 for the roller assembly 30, the guide wire 22 (or portion thereof) positioned within the clearance device 14, as well as other internal components.

The housing 32 defines an interior 34 and an exterior 36, and a port 38 for providing access to the interior 34 of the housing 32. The guide wire 22 can reside at least partially within the housing 32, and can be translated through the port 38 of the housing 32 to advance or retract the guide wire 22 within the medical tube 12. In the illustrated embodiment, the housing 32 includes a first shell half 40 and a second shell half 42 that can be (optionally removably) connected to each other to seal the interior 34 from the exterior 36, forming an enclosure. In particular, the shell halves 40, 42 are connected together with fasteners (e.g., screws), and a seal member (e.g., gasket, adhesive) is provided between the shell halves 40, 42 along their seam to inhibit fluid communication through the seam. However, the housing 32 may consist of a single shell or more than two shell components in other examples. It is to be appreciated that the shell components can be permanently or non-permanently secured together in any desired manner. For instance, two or more shell components can be connected via welding, such as ultrasonic welding, induction welding, laser welding, etc. or sealed by extruded-bead sealing or via suitable adhesives.

Figure 3:
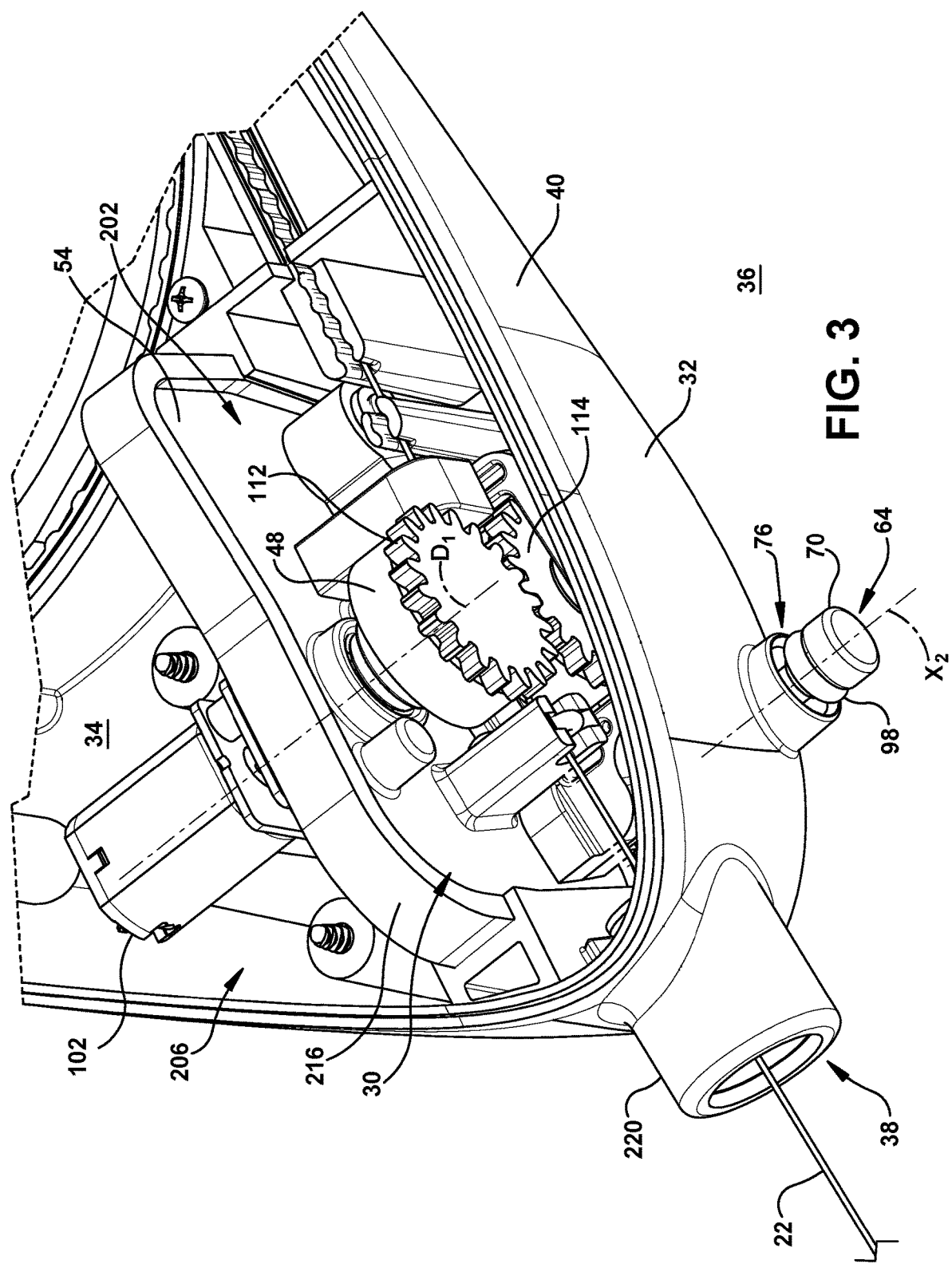
FIG. 3 is an enlarged view of a roller assembly of the clearance device, with an upper housing portion of the clearance device removed.
Figure 4:
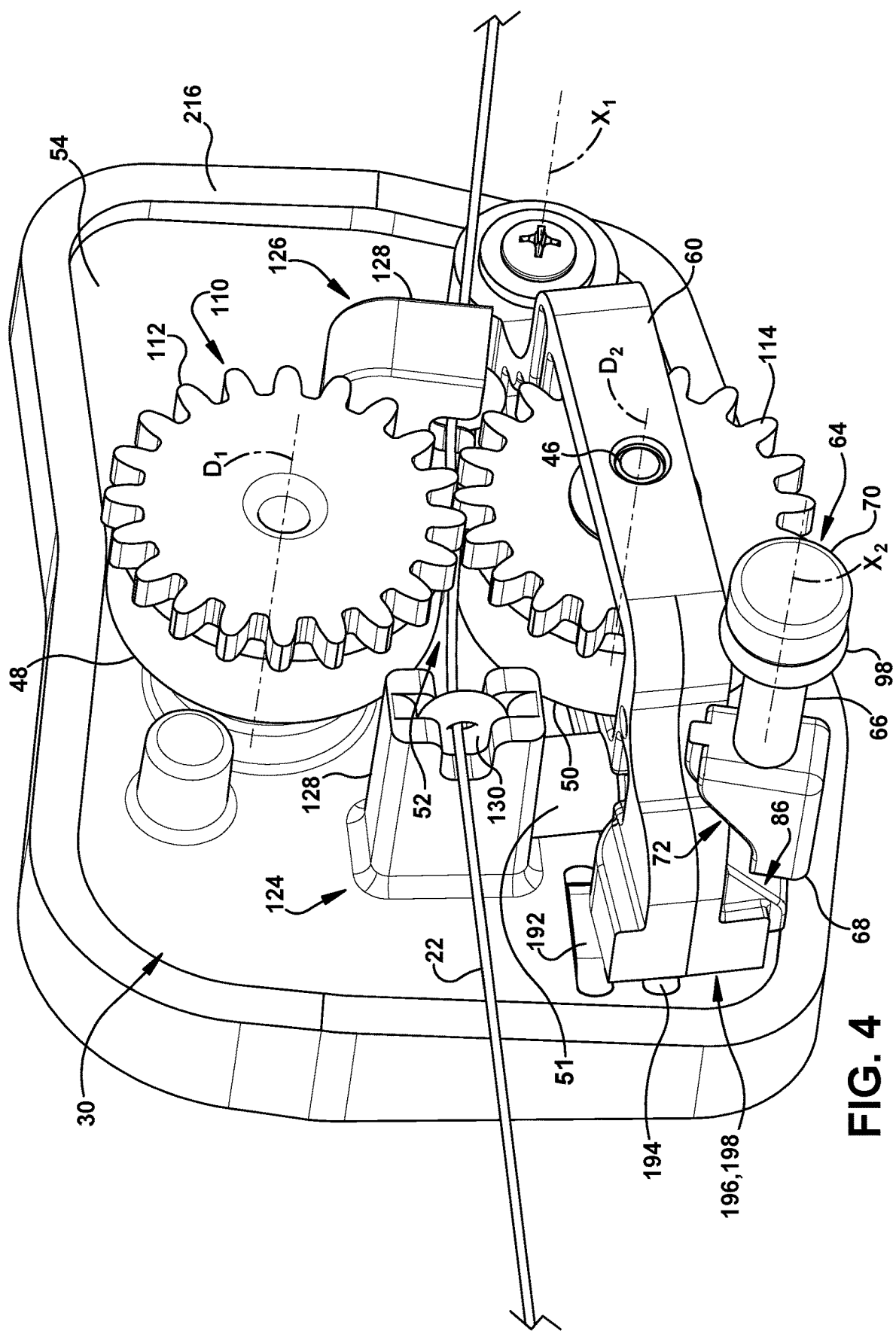
FIG. 4 is a perspective view of the roller assembly, with the entire housing of the clearance device removed.
Figure 5:
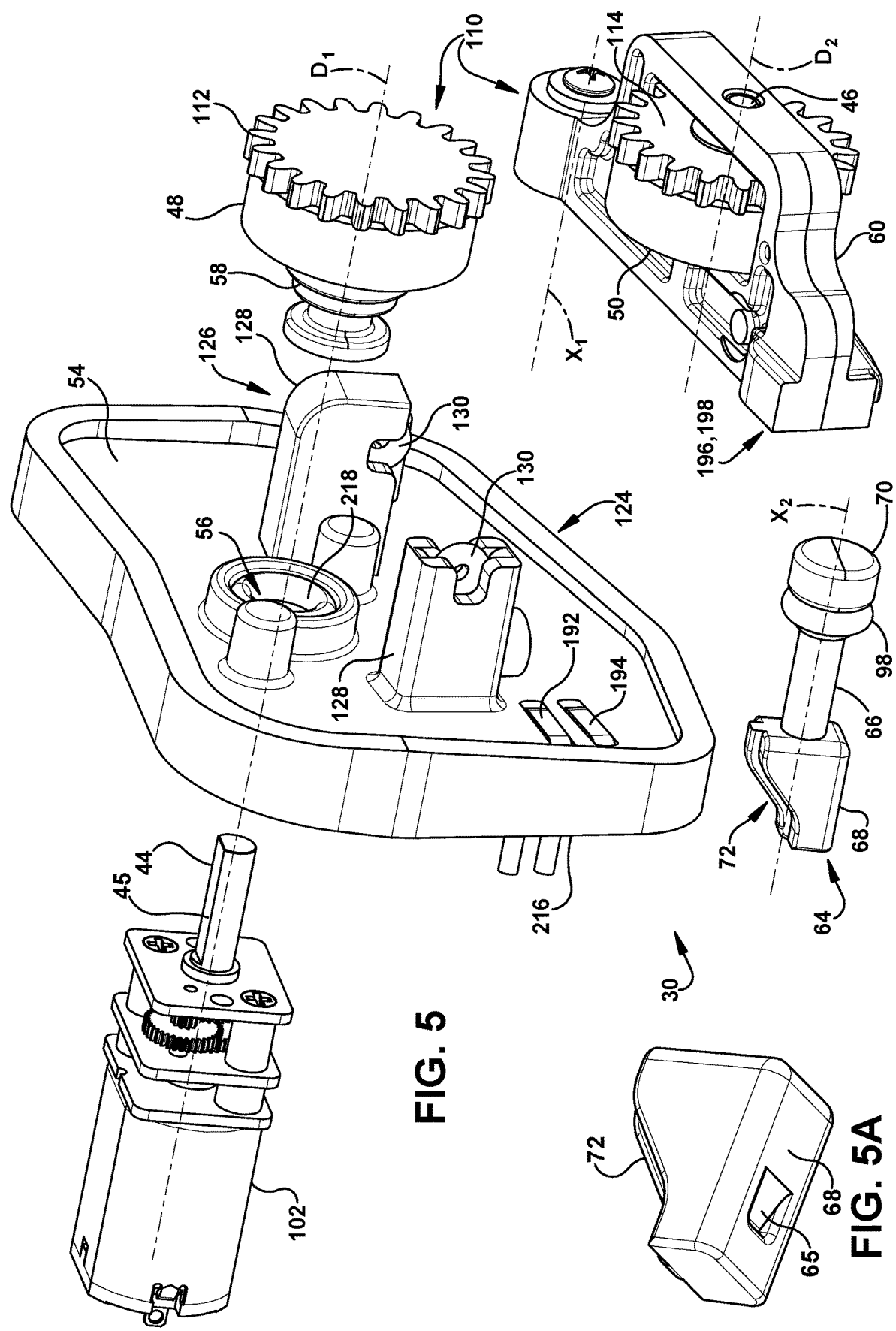
FIG. 5 is an exploded view of the roller assembly.

With reference now to FIGS. 3-5, the roller assembly 30 will be described in further detail. FIG. 3 shows a close-up of the roller assembly 30 within the housing 32, FIG. 4 shows the roller assembly 30 separated from the housing 32, and FIG. 5 shows an exploded view of the roller assembly 30.

The roller assembly 30 includes a first roller shaft 44 and a second roller shaft 46 (best seen in FIG. 5) that respectively define a first roller axis $D_1$ and a second roller axis $D_2$. The roller shafts 44, 46 are rotatable about their respective axes $D_1$, $D_2$. Moreover, the roller shafts 44, 46 are arranged such that respective axes $D_1$, $D_2$ are spaced apart and substantially parallel to each other.

The roller assembly 30 further includes first and second rollers 48, 50 respectively fixed to the first and second roller shafts 44, 46 such that the rollers 48, 50 are rotatable with the roller shafts 44, 46 about their respective axes $D_1$, $D_2$. In particular, the first roller 48 is fixed to and coaxial with the first roller shaft 44, and the second roller 50 is fixed to and coaxial with the second roller shaft 46.

Figure 13:
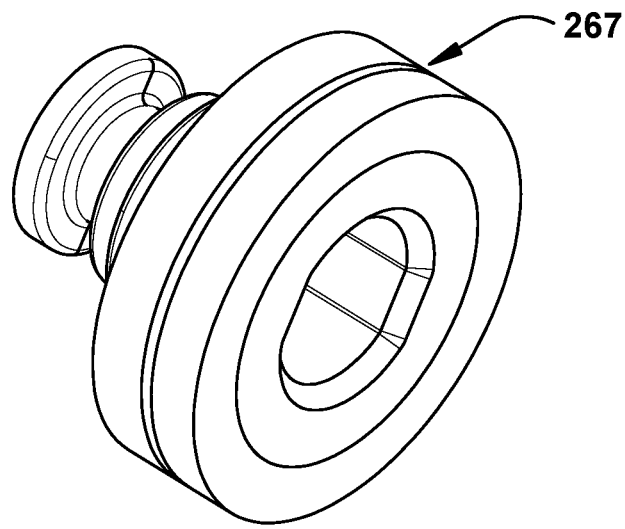
FIG. 13 is a perspective view of a roller that can be used in the roller assembly.
Figure 12:
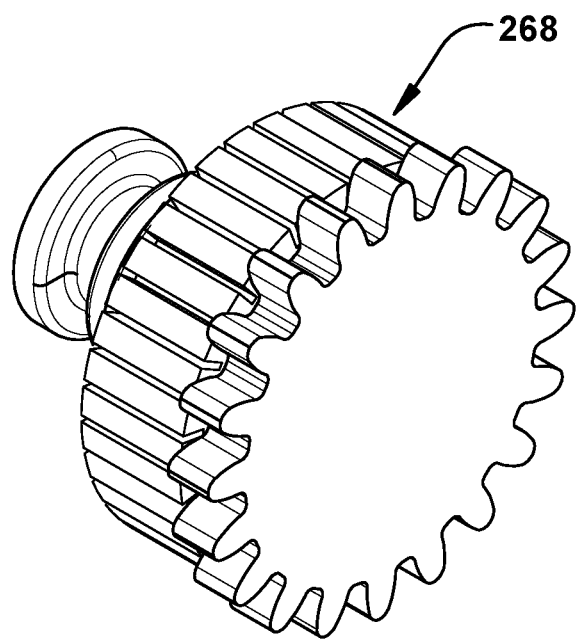
FIG. 12 is a perspective view of a roller that can be used in the roller assembly.

The first and second rollers 48, 50 can be axially aligned such that the outer circumferential surfaces of the rollers 48, 50 face each other and define a nip 52 therebetween (see FIG. 4). Moreover, the guide wire 22 can be arranged such that the guide wire 22 extends through the nip 52 and is engaged by (e.g. squeezed between) the rollers 48, 50. In this manner, the rollers 48, 50 can be rotated about their respective axes $D_1$, $D_2$ in opposite directions to drive the guide wire 22 through the nip 52 in either direction depending on the directions of rotation of the rollers 48, 50, to thereby advance or retract the guide wire 22 within the medical tube 12. Preferably, at least one of the rollers 48, 50 is coated with, or its respective circumferential surfaces is provided as, urethane or some other high-friction material to increase friction between the rollers 48, 50 at their nip, to aid in driving the guide wire 22 through the nip 52 to facilitate translation of the guide wire 22 through the medical tube 12. In addition or alternatively, the rollers 48, 50 themselves may comprise urethane or some other high-friction material. For instance, at least one of the rollers 48, 50 can be overmolded with urethane or other high friction material(s). A variety of different materials and/or coatings may be used for the rollers 48, 50 without departing from the scope of this disclosure. At least one of the rollers 48, 50 can comprise a rigid material, such as plastic or metal that is not necessarily a high friction material, while the opposing roller is (or has a coating of) high-friction or compressive material that can be pressed against the rigid-material roller to define a high-friction nip 52. Additionally, as shown in FIGS. 12 and 13, at least one of the rollers 48, 50 can include features to improve gripping, such as treads, radial lugs, ribs, grooves, etc. FIG. 13 illustrates a roller having a circumferential groove 267 therein. One or both rollers 48, 50 can include one or more than one such circumferential groove to maintain the guide wire 22 within the nip 52 and to mitigate any walking or drifting of the guide wire 22 laterally within the nip 52. The circumferential groove(s) can also facilitate gripping of the guide wire 22 within the nip 52. FIG. 12 illustrates a roller having a tread pattern 268 around a circumference thereof. As noted above, the tread pattern 268 facilitates gripping of the wire 22 between the rollers 48, 50. Any other suitable tread configuration or other pattern can be provided around at least a portion of the circumference of at least one of the rollers 48, 50 to improve gripping of the wire 22 within the nip 52.

The roller shafts 44, 46 and rollers 48, 50 can be rotatably coupled to the housing 32 in a variety of ways. For instance, with respect to the first roller shaft 44 and first roller 48, the roller assembly 30 can include a wall 54, bracket, or the like, fixed within the housing 32, wherein the wall 54 defines a roller shaft opening 56 for the first roller shaft 44 (see FIG. 5). The first roller shaft 44 can extend through the opening 56 such that it is rotatable within the opening 56. Moreover, one or more features can be provided to inhibit axial movement of the first roller shaft 44 through the opening 56. For example, one or more collars 58 can be fixed on the first roller shaft 44 (e.g., via set screws, being integral to the first roller shaft 44), and can be sized to interfere with axial movement of the first roller shaft 44 through the opening 56. In addition or alternatively, one or more snap rings can be snapped into corresponding annular grooves along the first roller shaft 44, and can also be sized to interfere with axial movement of the first roller shaft 44 through the opening 56. Alternatively, or additionally, one or more collars 58 can be press fit onto the first roller shaft 44, with or without adhesive and/or the first roller shaft 44 can be staked to maintain the collar(s) within a predetermined portion of the first roller shaft 44. Alternatively, or additionally, the first roller shaft 44 can be press fit onto the roller 48, with or without adhesive. The first roller shaft 44 can include at least one key feature, such as flat 45 shown in FIG. 5, in order to mitigate slippage of the collar(s), roller 48, and any other components coupled to the first roller shaft 44.

With respect to the second roller shaft 46 and second roller 50, the roller assembly 30 can include a carriage 60 that rotatably supports the second roller shaft 46, such that it is rotatable relative to the carriage 60 about the second roller axis $D_2$. The carriage 60 can be movably coupled to the wall 54 of the roller assembly 30 such that the carriage 60 is movable relative thereto. For example, the carriage 60 in the illustrated embodiment is pivotally coupled to the wall 54 such that the carriage 60 is pivotable about a carriage axis $X_1$ that is spaced from and substantially parallel to the second roller axis $D_2$. Alternatively or additionally, the carriage 60 can be linearly translating, e.g., vertically or horizontally moveable within the housing 32.

The movable carriage 60 enables the second roller shaft 46 and second roller 50 coupled thereto to be moved relative to the first roller shaft 44 and first roller 48 to vary the spacing between the first and second rollers 48, 50. In particular, the carriage 60 can be moved (e.g., pivoted about the carriage axis $X_1$) in order to move the second roller 50 into a disengaged position wherein the rollers 48, 50 are spaced apart to establish a clearance between the guide wire 22 and one or both rollers 48, 50. Conversely, the carriage 60 also can be moved (e.g. pivoted about axis $X_1$) into an engaged position wherein the rollers 48, 50 are closer to each other and appropriately distanced (and possibly contacting one another) to engage the guide wire 22 at the nip 52 defined therebetween. Thus, the second roller 50 can interact with the first roller 48 in the engaged position to drive the guide wire 22 through the nip 52 therebetween. Whereas, in a disengaged position as described above, no such interaction occurs. It is to be appreciated that the engaged position can include a position where the rollers 48, 50 are in contact with one another, such as via a slip fit or interference fit, in which the rollers 48, 50 are compressed against and around the guide wire 22. Meanwhile, the second roller 50 can be spaced from the first roller 48 in the disengaged position to disable interaction of first and second rollers 48, 50. FIG. 4 illustrates the carriage 60 and second roller 50 in a disengaged position, with the wire 22 passing between, but not being forcibly engaged by, the opposing circumferential surfaces of the rollers 48, 50.

The roller assembly 30 can be initially configured with the carriage 60 in its disengaged position. This initial configuration is particularly advantageous if the clearance device 14 will be stored for an extended period of time before use, so that the rollers 48, 50 are not persistently engaged with the guide wire 22 during storage, which could negatively affect the guide wire 22 and/or rollers 48, 50. Moreover, the carriage 60 may be spring loaded in the open position (disengaged) so that forces experienced during shipping, etc., do not unintentionally engage the carriage (rollers, power, etc.). The spring 51 can be made of various materials such as foam or steel wire coil. As illustrated in FIG. 4, the spring 51 is a foam cylinder positioned at the distal end of the carriage 60. When it is desirable to use the clearance device 14 for translating the guide wire 22, the carriage 60 can be moved from its disengaged position to its engaged position to enable driving of the guide wire 22 via the first and second rollers 48, 50. The clearance device 14 can include an actuator 64 that is operable to move the carriage 60 (and the second roller 50 coupled thereto) from its disengaged position to its engaged position. As discussed in further detail below, the actuator 64 can be movably coupled to the housing 32 such that the actuator 64 is accessible from the exterior 36 of the housing 32 and movable from a first position to a second position by a user from the exterior 36 thereof. Moreover, the actuator 64 can be configured to engage the carriage 60 as the actuator 64 is moved from its first position to its second position to move the carriage 60 from its disengaged position to its engaged position.

For instance, as shown in FIG. 4, the actuator 64 can include an actuator shaft 66 that defines an actuator axis $X_2$. Moreover, the actuator 64 can include a cam body 68 and a plug 70 that are provided on opposite ends of the actuator shaft 66. The plug 70 may be radially larger than the actuator shaft 66. Moreover, the cam body 68 has a cam surface 72 that is ramped relative to the actuator axis $X_2$ (i.e., the cam surface 72 extends in a direction oblique to the actuator axis $X_2$). The cam surface 72 can be curved (as shown in the illustrated embodiment), or the cam surface 72 can be planar.

Figure 6:
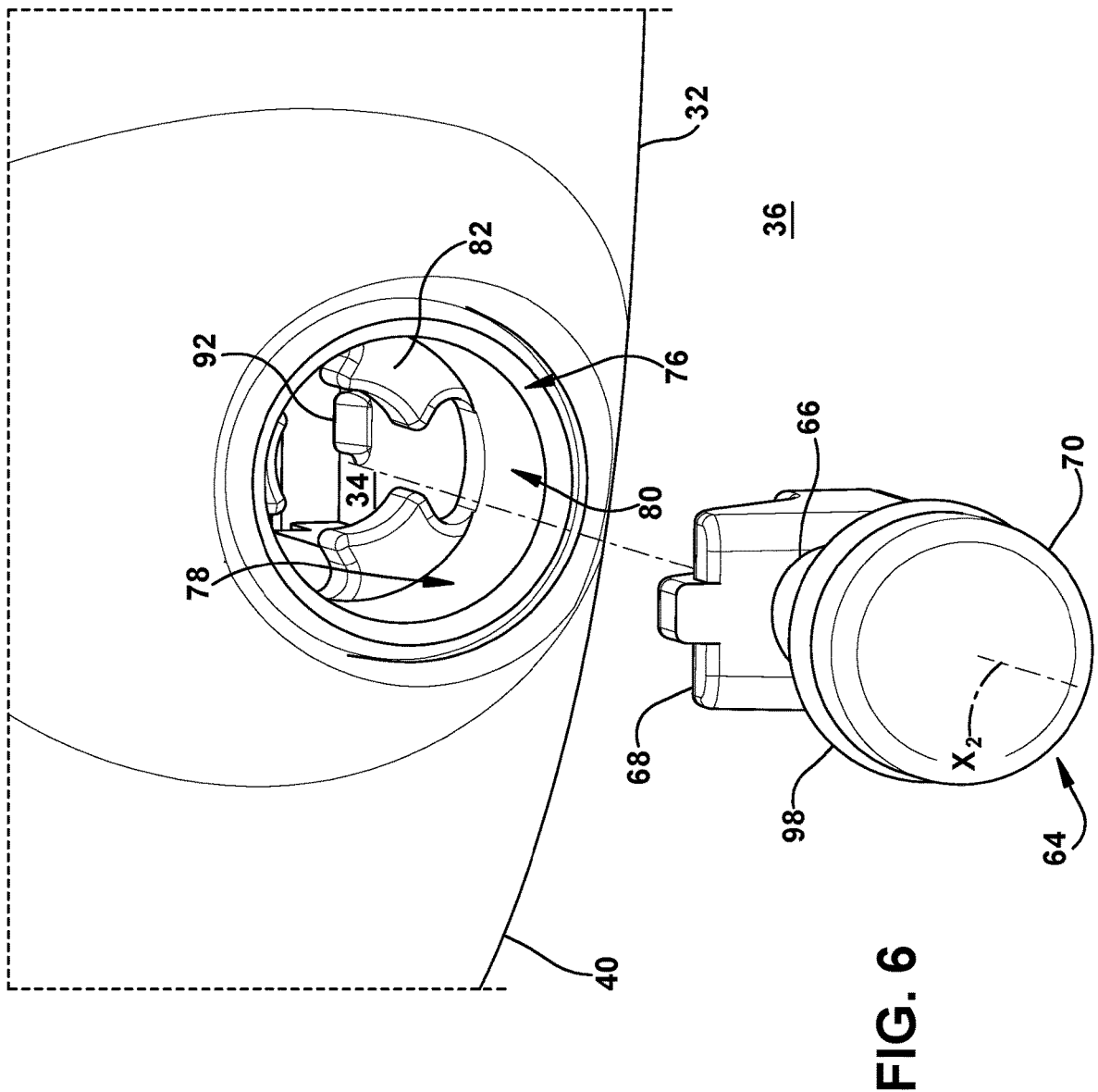
FIG. 6 is an enlarged view of an actuator of the clearance device, separated from a guide of the clearance device.

As further shown in FIG. 6, the clearance device 14 can include a guide passage 76 (e.g., formed in the housing 32) extending into the interior 34 of the housing 32 and configured to slidably receive the actuator 64. The actuator guide passage 76 has an inner surface 78 that defines a guide channel 80 extending through the guide passage 76 from the exterior 36 of the housing 32 to its interior 34. The actuator 64 can be slidably received within the guide passage 76 such that the actuator 64 is slidable through the guide channel 80 along the actuator axis $X_2$. In particular, the housing 32 can include one or more guide arms 82 that extend inward from the inner surface 78 of the guide passage 76 and slidingly engage the shaft 66 of the actuator 64 to hold and center the actuator 64 within the guide passage 76.

The actuator 64 can be arranged within the guide passage 76 such that its cam body 68 is aligned inward of its plug 70, with the cam body 68 being located on the inner side of the guide arms 82 and the plug 70 being located on the outer side of the guide arms 82. In this manner, the cam body 68 and plug 70 can limit axial movement of actuator 64 through the guide passage 76 in both directions.

The actuator 64 can be slid within the guide passage 76 along its actuator axis $X_2$ from a first position to a second position, the second position being further into the housing 32 along the actuator axis $X_2$ than the first position. More specifically, in the first position, the actuator 64 will be located along the actuator axis $X_2$ such that its plug 70 protrudes outwardly from, and optionally resides completely outside of, the guide channel 80 in the exterior 36 of the housing 32 (see e.g., FIG. 3). Meanwhile, in the second position, the actuator 64 will be advanced along the actuator axis $X_2$ such that the plug 70 has been advanced inward through the guide channel 80, and optionally that its outer surface is flush with the surrounding portion of the housing.

When the actuator 64 is in its first (withdrawn) position, the carriage 60 will assume its disengaged position. As the actuator 64 is moved (e.g., pushed or advanced) from its first position along the actuator axis $X_2$ into the housing 32, the cam surface 72 of the actuator 64 is designed to engage an associated mating surface 86 of the carriage 60 (see FIG. 4) and urge the carriage 60 from its disengaged position toward its engaged position, e.g. by pivoting the carriage 60 about the carriage axis $X_1$ or by translating the carriage 60 into position. For example, a cam may be used to translate the carriage vertically to engage the rollers.

The actuator 64 is advanced until the actuator 64 reaches its second position, at which point the carriage 60 will assume its engaged position. The carriage 60 may also be moved between its unengaged and engaged positions by action of a spring. For example, when a user engages the actuator 64, via a button or the like, the carriage 60, which can be spring loaded, is released. It is to be appreciated that if the carriage is spring loaded, this configuration can also be employed to maintain a predetermined compression force on the rollers 48, 50.

The clearance device 14 can include one or more features for locking the actuator 64 in its second position. For example, as shown in FIG. 6, the clearance device 14 can include a catch 92 (e.g., formed by the housing 32) that will mate with an associated recess 65 in the actuator 64 as the actuator 64 enters its second position, thereby locking the actuator 64 and inhibiting movement of the actuator 64 back toward its first position. In other examples, the catch 92 may be provided on the actuator 64 and a recess may be formed by the housing 32 that captures the catch 92 when the actuator 64 enters its second position. The actuator 64 may be locked in its second position in a variety of different ways without departing from the scope of the invention.

A seal member 98 is configured to establish a seal between the actuator 64 and the guide passage 76 based on the position of the actuator 64. For instance, the seal member 98 can be an O-ring provided on the actuator 64 and extending circumferentially about the plug 70 of the actuator 64. The seal member 98 can be configured such that when the actuator 64 is in its second position with the plug 70 residing at least partially within the guide channel 80, the seal member 98 will establish a seal between the plug 70 and the inner surface 78 of the guide passage 76, which inhibits fluid communication through the guide channel 80. Meanwhile, when the actuator 64 is in its first position with the plug 70 (and seal member 98 coupled thereto) residing out of the guide channel 80, in the illustrated embodiment fluid communication between the interior 34 and exterior 36 of the housing 32 will be permitted through the guide channel 80 between the actuator 64 and the inner surface 78 of the guide passage 76.

The selective seal described above enables a sterile field to be maintained in the housing 32 when the actuator 64 is in the second position and the rollers 48, 50 are engaged with the guide wire 22 and operable to advance or retract the guide wire 22. The selective seal also enables a pressure (i.e. vacuum) to be maintained in the housing 32 when the actuator 64 is in the second position. Conversely, when the actuator 64 is in its first position and the rollers 48, 50 are inoperable to advance or retract the guide wire 22, fluid communication between the interior 34 and exterior 36 of the housing 32 will be permitted through the guide channel 80. Such fluid communication can permit a sterilizing fluid (e.g., gas such as ethylene oxide) to be introduced and/or evacuated into and/or from the interior 34 of the housing 32 through the guide channel 80 for the purposes of sterilizing the interior 34. Alternatively, a seal can be provided such that the sterile field is maintained within the housing 32 when the actuator 64 is in either the first or second position. Fluid communication between the interior 34 and exterior 36 of the housing 32 can be accomplished via one or more separate vent features, as desired.

The actuator 64 in the illustrated embodiment is designed such that the actuator 64 will be locked in its second position (i.e., via catch 92) once moved thereto, and will not be returnable to its first position. However, in other examples, the actuator 64 can be releasable from its locked state and returnable to its first position, to return the carriage 60 to its disengaged position and (in select embodiments) enable fluid communication through the guide channel 80 for a sterilizing fluid to be introduced and/or evacuated into and/or from the housing 32.

Referring back to FIG. 5, one or both the first and second rollers 48, 50 can be driven by a motor. For instance, in the illustrated embodiment the roller assembly 30 includes a single motor 102 that is coupled to the first roller shaft 44 on an opposite side of the partition wall 54 from the first roller 48. The motor 102 is operable to rotate the first roller shaft 44 and first roller 48 at a fixed or variable speed, to facilitate driving the guide wire 22 in both forward and reverse directions. The motor 102 preferably is a DC brushed gear motor, although other motors or drive mechanisms, such as a belt driven shaft, are possible in other examples. Moreover, it is to be appreciated that a similar motor may be similarly coupled to the second roller shaft 46 to rotate the second roller 50, in addition or as an alternative to the motor 102 coupled to the first roller shaft 44.

In some embodiments, one of the rollers 48, 50 can be rotated by a motor or other drive mechanism, while the other of the rollers 48, 50 is configured to passively rotate in response to rotation of the driven roller due to the frictional engagement between the rollers 48, 50 and the intermediate guide wire 22 extending through the nip therebetween (if present). For example, the first roller 48 can be driven by the motor 102 described above while both rollers 48, 50 are engaged with the guide wire 22. Such rotation of the first roller 48 will exert a tangential force on the guide wire 22 that causes the guide wire 22 to translate through the nip 52 between the rollers 48, 50. The second roller 50, in turn, can passively rotate in response to translation of the guide wire 22 (or to rotation of the first roller 48, or both) due to its frictional engagement therewith. Likewise, if the rollers 48, 50 are in direct contact, rotation of the driven roller will directly rotate the passive roller. The passive roller may include a bearing or similar structure in order to reduce friction and thus, power consumption.

In other embodiments, the clearance device 14 can include a transmission that enables both rollers 48, 50 to be driven by a single motor (or other drive mechanism) in a synchronized manner. For instance, as shown in FIGS. 4 and 5 the roller assembly 30 includes a transmission 110 having a first gear 112 that is coaxial with and fixed to the first roller shaft 44 such that the first gear 112 is rotatable with the first roller shaft 44 about the first roller axis $D_1$. The transmission 110 further includes a second gear 114 that is coaxial with and fixed to the second roller shaft 46 such that the second gear 114 is rotatable with the second roller shaft 46 about the second roller axis $D_2$. The first and second gears 112, 114 of the transmission 110 are meshed with each other such that rotation of the first roller shaft 44 (e.g., via the motor 102) in one direction (e.g., clockwise) is transmitted into rotation of the second roller shaft 46 in an opposite direction (e.g., counter-clockwise). However, the transmission 110 may include intermediate gears between the first and second gears 112, 114 in other examples such that the first and second gears 112, 114 are not directly meshed with each other but nonetheless transmit rotation therebetween via the intermediate gears.

The transmission 110 is thus configured to synchronize rotation of the first and second roller shafts 44, 46 (and the first and second rollers 48, 50 coupled thereto) about their associated roller axes $D_1$, $D_2$ in opposing directions. Preferably, in embodiments wherein the rollers 48, 50 are substantially similar in diameter, the transmission 110 is configured to synchronize rotation of the rollers 48, 50 with a 1:1 ratio of angular velocities. However, other ratios of angular velocities are possible in other embodiments, particularly embodiments wherein the rollers 48, 50 have different diameters where it may be desirable to ensure constant lineal velocities between their respective circumferential surfaces at the nip therebetween, resulting in unequal rotational velocities.

The two-roller assembly described herein is only an example of a configuration that can be employed to grip and feed the guide wire 22 through the device 14. For instance, the device may include two sets of rollers positioned adjacent or near each other. Alternatively, the guide wire can be fed through a three roller system with one driven roller and two passive rollers. It is to be appreciated that any suitable configuration can be employed and is contemplated as falling within the scope of the present disclosure.

Figure 7:
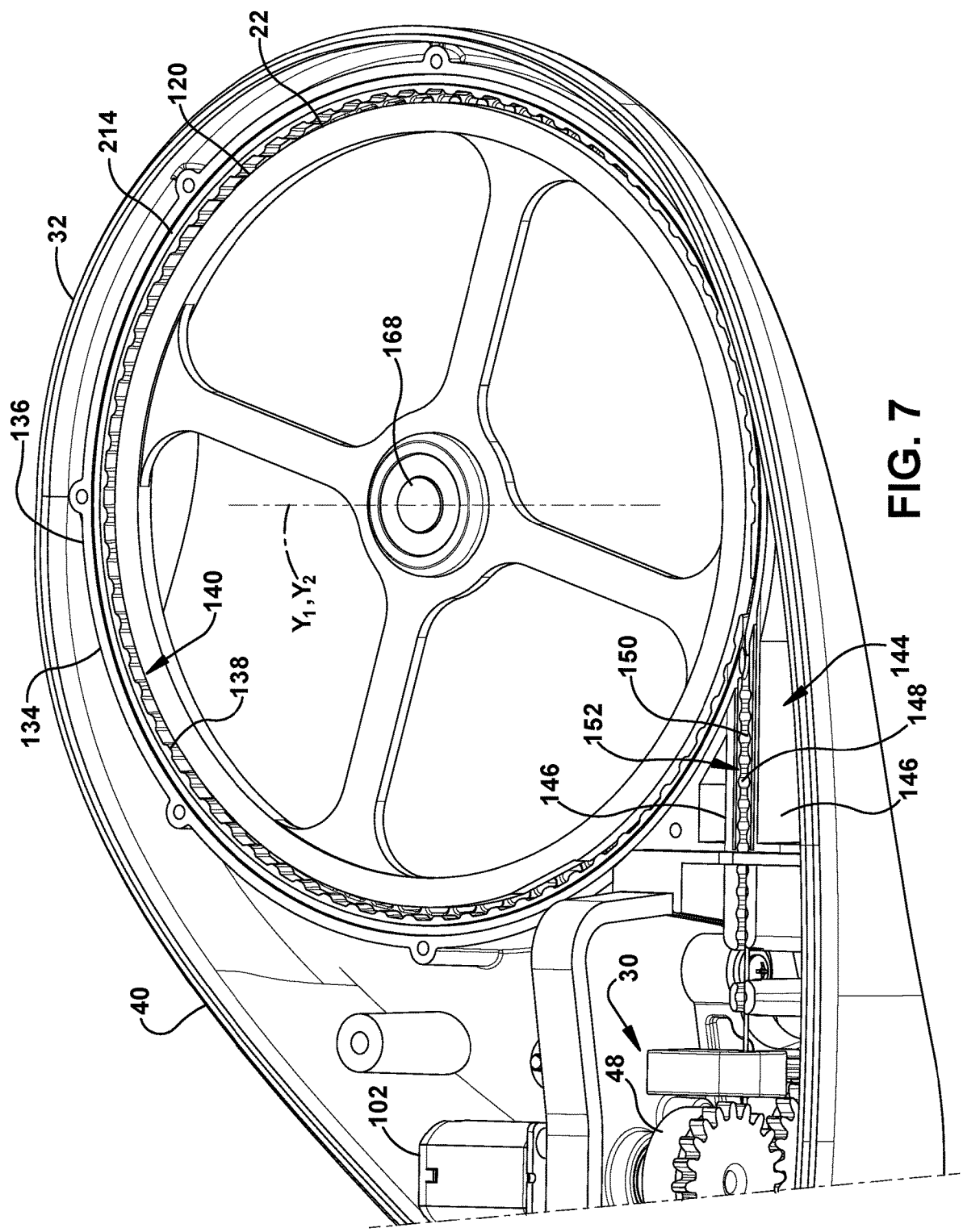
FIG. 7 is an enlarged view showing a spool of the clearance device, with an upper housing portion of the clearance device removed.

Turning to FIG. 7, the clearance device 14 can include a spool 120 within the housing 32 for dispensing and accumulating the guide wire 22 as the guide wire 22 is advanced or retracted through the port 38 (and hence the medical tube 12) by the roller assembly 30. The spool 120 can be rotatably coupled to the housing 32 such that the spool 120 is rotatable relative to the housing 32 about a spool axis $Y_1$. Optionally, as shown in FIG. 7A, the spool 120 can be rotatably coupled in a bearing 121 within the housing 32 such that the spool 120 is rotatable relative to the housing about the spool axis $Y_1$. Moreover, the guide wire 22 can be fixed to the spool 120 at its proximal end and wrapped at least partially about the spool 120 circumference, with a free portion of the guide wire 22 feeding off of the spool 120 and through the nip 52 between the first and second rollers 48, 50. The spool 120 can be configured to freely rotate relative to the housing 32 such that the spool 120 passively rotates about its spool axis $Y_1$ in response to compressive and tensile forces in the guide wire 22 as it is driven through the nip 52. More specifically, as the roller assembly 30 is operated to advance the guide wire 22 through the nip 52 and into the medical tube 12, the spool 120 can passively rotate to dispense the guide wire 22 off of the spool 120 and to the nip 52. Conversely, as the roller assembly 30 is operated to retract the guide wire 22 through the nip 52 from the medical tube 12, the spool 120 can passively rotate to accumulate the guide wire 22 from the nip 52 and onto the spool 120.

However, it is to be appreciated that the spool 120 may be actively driven in other embodiments to accumulate or dispense guide wire 22 length as the guide wire translates through the nip 52. For instance, as shown in FIG. 8, the transmission 110 described above may be further configured so that the motor 102 drives the spool 120 in a synchronized manner with the rollers 48, 50 to dispense or accumulate the guide wire 22 as the guide wire translates through the nip 52. In particular, the transmission 110 can include one or more additional gears 122 that are configured to transmit rotation of the first roller shaft 44 by the motor 102 into synchronized rotation of the spool 120.

The clearance device 14 can include one or more guide features within its housing 32 for directing the guide wire 22 through the nip between the rollers 48, 50 and about the spool 120, as will now be described in further detail.

For example, as shown in FIGS. 4 & 5, the roller assembly 30 can include a distal wire guide 124 and a proximal wire guide 126 arranged on opposite sides (e.g., distal and proximal sides) of the roller nip 52 that are configured to keep the guide wire 22 centered through the nip 52 of the rollers 48, 50. Each wire guide 124, 126 can include a support body 128 that is fixed within the housing 32; for example to the partition wall 54 of the roller assembly 30 as shown. Moreover, each wire guide 124, 126 can include a guide ring 130 that is fixed to and supported by its support body 128. In particular, each support body 128 can be fixed to the partition wall 54 within the housing 32, and each guide ring 130 can include a Teflon O-ring, as shown in the illustrated embodiment. The guide wire 22 can be fed through the guide rings 130 of the distal and proximal wire guides 124, 126, which will center the guide wire 22 through the nip 52 of the rollers 48, 50. In this preferred configuration, each guide ring 130 reduces contact with the guide wire 22, which results in reduced friction and reduced resistance to winding as the guide wire 22 is advanced or withdrawn.

As another example, the clearance device 14 can include a guide wall 134 (see FIG. 7) that extends at least partially about the circumference of the spool 120, which can constrain the guide wire 22 about the spool 120 and ensure that the guide wire 22 resides in close proximity to spool 120 about its circumference. In particular, the guide wall 134 can be a circular wall defining a circular recess at its center whose diameter approximates that of the spool 120, within which the spool 120 may be seated so that the outermost portion of the spool opposes the guide wall 134 about the spool circumference. The guide wall 134 preferably is a curved wall with an axis of curvature $Y_2$ that is coaxial to the spool axis $Y_1$. Moreover, the guide wall 134 can be defined by the housing 32 or some other portion fixed within the housing 32.

In some examples, the guide wall 134 may have a smooth and continuous inner surface that faces and extends about the spool 120. In the illustrated embodiment, the guide wall 134 includes a rim 136 and a plurality of guide projections 138 that extend radially inward from the rim 136 toward the spool 120 and are circumferentially spaced about the spool 120, the guide projections 138 being separated by intermediate wall recesses 140. The alternating projections 138 and wall recesses 140 can reduce the total amount of surface contact between the guide wall 134 and guide wire 22 (as compared to a guide wall 134 with a smooth and continuous inner surface), thereby reducing the amount of frictional resistance the guide wall 134 exerts on the guide wire 22 as the guide wire 22 is dispensed from or accumulated about the spool 120. Lubricants, coatings and other mechanisms and techniques for reducing friction forces can also be used in the device. Lubricants and coatings may include PTFE, FEP, silicone or other oils, etc.

As yet another example, the clearance device 14 can include a guide conduit 144 (also shown in FIG. 7) defining a confined path within the housing 32 for directing the guide wire 22 between the spool 120 and roller assembly 30. The guide conduit 144 can include a pair of conduit walls 146 (e.g., defined by the housing 32) that extend substantially parallel to each other and define a conduit channel 148 therebetween for the guide wire 22. In the illustrated embodiment the guide conduit 144 extends substantially tangentially from the guide wall 134 and the spool circumference so that the guide wire 22 can follow a smooth path through the conduit 144 as it is being dispensed from or accumulated on the spool 120. The guide conduit 144 can further include a plurality of guide projections 150 that extend from each conduit wall 146 into the conduit channel 148, and which are spaced along the conduit channel 148 to define a plurality of conduit recesses 152 therebetween. Similar to the guide projections 138 and wall recesses 140 of the guide wall 134 described above, the alternating guide projections 150 and conduit recesses 152 of the conduit walls 146 can reduce the total amount of surface contact between the guide conduit 144 and guide wire 22, thereby reducing the amount of frictional resistance the guide conduit 144 may assert on the guide wire 22 as the guide wire 22 translates through the guide conduit 144.

Figure 14:
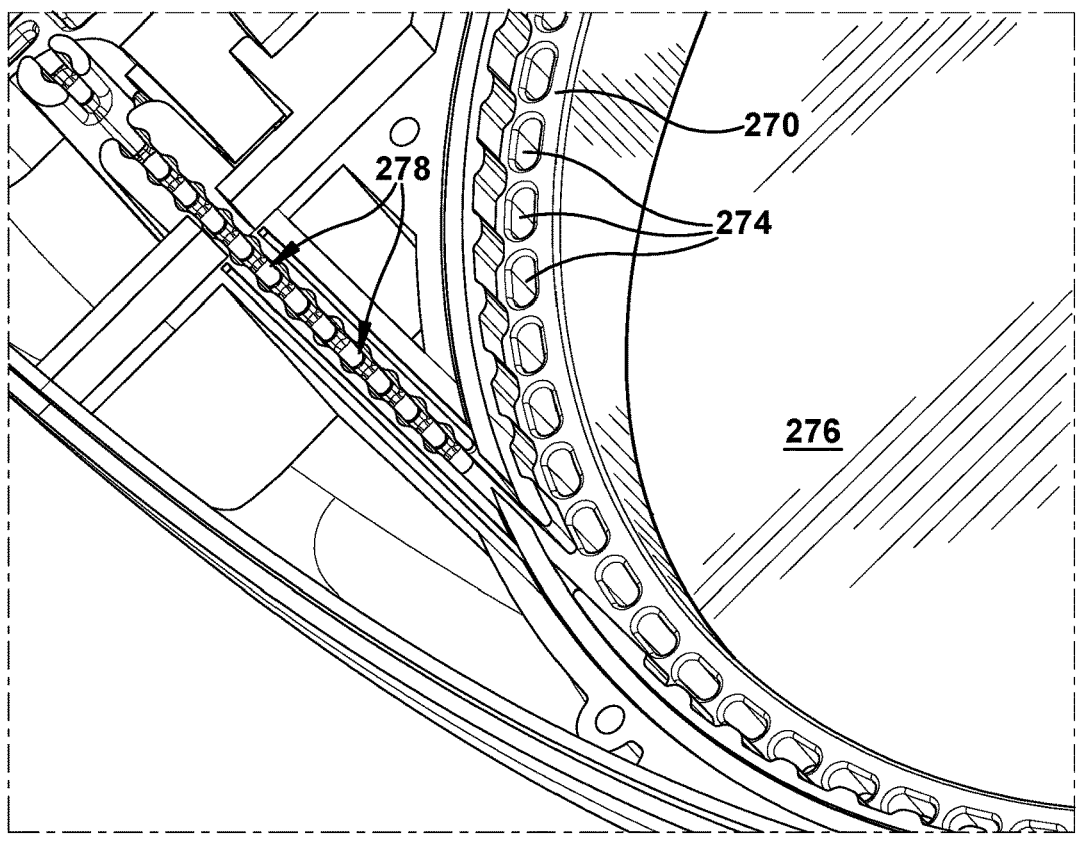
FIG. 14 is a partial perspective view of a spool compartment of a clearance device.

As shown in FIG. 14, similar to the guide projections 138, 150 and wall/conduit recesses 140, 152 in the guide wall 134 and conduit walls 146 that reduce contact area and thus friction forces, a shelf 270 of a spool compartment 276 includes a plurality of recesses 274. Similar recesses can also be provided on an opposing surface (not shown) of the cover plate 210 (FIG. 2), which provide reduced surface contact with the spool 120. The recesses reduce surface area of contact, and thus, friction forces. In other words, when the spool 120 rotates between the shelf 270 and the cover plate 210, the reduced surface contact between the spool 120, shelf 270, and cover plate 210 provided by the recesses 274 in both the shelf 270 and cover plate 210 results in reduced friction and reduced resistance to rotation of the spool 120. Further, when the spool 120 rotates between the shelf 270 and the cover plate 210, the reduced surface contact between the guide wire 22, shelf 270, and cover plate 210 provided by the recesses 274 in both the shelf 270 and cover plate 210 results in reduced friction and reduced resistance to rotation of the spool 120. The shelf 270, guide wall 134, spool 120 and cover plate 210 define the spool compartment 276 in which the guide wire 22 is contained during spooling and unspooling. The recesses 274 on the shelf 270 can also serve to collect any debris or particulate that might be carried into the compartment 276 on the wire 22, such as dried blood. For example, dried blood residue may be carried into the spool compartment 276 via the guide wire 22, which may be removed from the guide wire 22 when it is wound on the spool 120. The dried blood residue may collect in the recesses 274 so as to be removed from moving surfaces. Similar recesses 278 (i.e. illustrated in FIG. 14) can also be provided in the guide conduit 144 that leads into the spool compartment 276 as well as other areas of wire contact. In another embodiment, the plurality of recesses 274 of the shelf 270 may be replaced with guide projections, similar to the guide projections 138 and 150 in the guide wall 134 and conduit walls 146, respectively. Such projections on the shelf would reduce surface contact between the spool 120 and the shelf, which leads to reduced friction and reduced resistance to rotation of the spool 120. In another embodiment, the guide projections 138 and wall recesses 140 in the guide wall 134 may be replaced with recesses, similar to the recesses 274 of the shelf 270. These recesses would reduce surface contact between the guide wire 22 and the guide wall 134, which leads to reduced friction and reduced resistance to rotation of the spool 120. As noted above, lubricants, coatings and other mechanisms and techniques for reducing friction forces can also be used in the device. Lubricants and coatings may include PTFE, FEP, silicone or other oils, etc.

Figure 15:
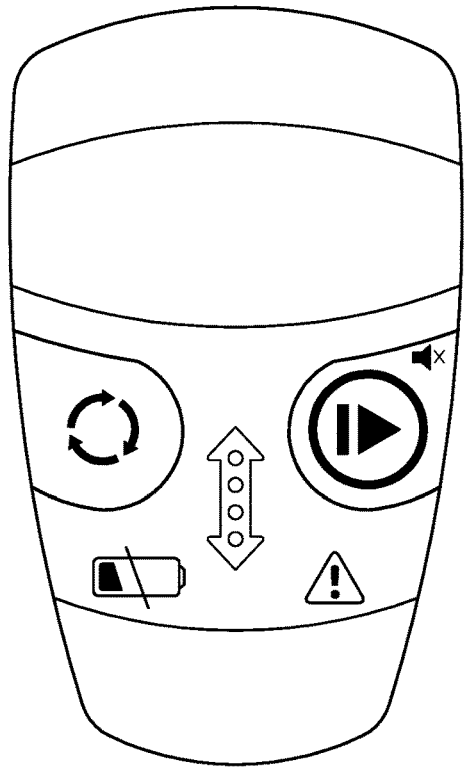
FIG. 15 is an example user interface for a clearance device.

Referring back to FIG. 2, the clearance device 14 can include a control system 160 configured to control operation of the roller assembly 30 (e.g., via the motor 102) to advance or retract the guide wire 22. In particular, the control system 160 can include a controller 162 such as a microprocessor that is in communication with the motor 102 and can selectively operate the motor 102 to rotate the first and second rollers 48, 50 and translate the guide wire 22 through the nip 52. The control system 160 can further include a user interface 164 in communication with the controller 162 that enables a user to interact with the control system 160 to control operation of the roller assembly 30. The user interface 164 can include a display, a touch-screen, one or more switches or buttons, or any other feature that enables a user to interact with the control system 160 and control operation of the roller assembly 30. The display can supply information to the user, such as position of the clearance member(s) 24, direction of travel, etc. One example of a user interface is shown in FIG. 15.

The controller 162 can be configured to operate the roller assembly 30 to advance or retract the guide wire 22 according to one or more predetermined stroke cycles. A 'stroke' can correspond to an actuation of the guide wire 22 from an advanced state to a retracted state and back to the advanced state. Alternatively, a stroke can correspond to an actuation of the guide wire 22 from a retracted state to an advanced state and back to the retracted state. In a further alternative, a stroke can correspond to actuation of the guide wire 22 only between the retracted and advanced states, or vice versa. The precise scope of actuation of the guide wire 22 constituting a stroke in a particular case may be determined in the judgment of the clinicians responsible for patient care. In that regard, a 'stroke' as used here can refer to any movement or sequence of movements of the guide wire 22, via advancement or retraction thereof through the nip 52, that can be executed by operation of the motor 102 (or motors if more than one is used) at successive or user-selected time intervals, or at selected moments in time.

The controller 162 can be configured to stroke the guide wire 22 according to a predetermined stroke cycle. For instance, in one example stroke cycle, the guide wire 22 can be stroked intermittently for a set number of strokes within a set period of time, wherein the time interval between strokes can be controlled. In another example, the guide wire 22 can be stroked continuously for a set number of strokes with no or substantially no time interval between strokes. In yet another example, the guide wire 22 can be stroked a single time, for example on demand based on a user input. The controller 162 can be configured to stroke the guide wire 22 according to a variety of different stroke cycles.

The user interface 164 can enable a user to initiate and/or terminate a stroking operation of the guide wire 22. Moreover, the user interface 164 can enable a user to adjust the parameters of a predetermined stroke cycle such as, for example, how many times the guide wire 22 should be stroked, the time interval between strokes, a position of the guide wire 22 in the retracted state, or a position of the guide wire 22 in the advanced state. The interface 164 further can enable the user to select the speed at which the guide wire 22 is stroked; i.e. the speed at which it is advanced and/or retracted into/from the medical tube. Still further, the user interface 164 can display one or more operating parameters of a stroking operation such as, for example, the current position and/or direction of the guide wire 22, the current position and/or direction of the clearance member(s) 24, whether the guide wire 22 and clearance member(s) 24 are moving or stationary, the speed of the guide wire 22 and clearance member(s) 24, and cycle indicators, such as the number of completed strokes, or the duration for which a stroking operation has been running.

In some embodiments, the control system 160 can include one or more sensors for detecting one or more operating parameters of the clearance device 14. For instance, as shown in FIGS. 2 and 7 the clearance device 14 can include a magnet 168 that is fixed to the spool 120 such that the magnet 168 is rotatable with the spool 120 about the spool axis $Y_1$. Meanwhile, the control system 160 can include an encoder 170 (e.g. a Hall effect sensor) that is configured to detect a rotary position of the magnet 168 about the spool axis $Y_1$. In this manner, the control system 160 can detect the rotary position and/or number of revolutions or rotational speed or direction of the spool 120 about the spool axis $Y_1$, which can indicate the degree to which the guide wire 22 has been advanced or retracted, the current direction state of its movement, its rate (speed) of advancement or withdrawal, etc. Notably, many of these same parameters can be detected by inference based on the rotational speed of the rollers 48, 50. The rotational speed of the roller can be measured directly or can be inferred based on operation of the motor 102. By comparing the rotational speed of the rollers 48, 50 with the measured rotational speed and other parameters of the spool 120, certain faults may be detected in order to generate an alarm or other output. For example, if the guide wire 22 is stuck due to obstruction in the medical tube 12 and therefore is not moving despite operation of the rollers 48, 50, the spool 120 will not move, and thus the spool 120 will not rotate. Mis-matched rotations detected between the rollers and the spool can be used to trigger an obstruction alarm to notify clinicians that corrective action is required.

In addition or alternatively to the encoder 170, the control system 160 can include various other types of sensors that detect other types of parameters such as, for example, the rotary position of the first roller 48 and/or second roller 50, the duration in which the motor 102 has been operated, or a torque being applied to the first roller shaft 44 and/or second roller shaft 46. The control system 160 can include a variety of different sensors without departing from the scope of this disclosure. Such sensors can be used to detect parameters and generate data that can be used by the controller or by a remote computer (e.g. linked via cable or wirelessly) to infer clinical conditions. For example, the torque required to drive the guide wire 22 past an obstruction may be used to infer the composition or other features of the obstruction. The torque profile as the guide wire 22 is being advanced or withdrawn through the medical tube 12 may be used to infer the location of an obstruction within that tube, which might not otherwise be visible because it is located within a portion of the tube located inside a patient's body.

The sensor(s) of the control system 160 can be in communication with the controller 162, which can be configured to selectively operate the roller assembly 30 based on the operating parameter(s) detected by its sensor(s). For instance, the controller 162 can be configured to operate the roller assembly 30 based on the rotary position detected by the encoder 170 described above. In particular, a predetermined stroke cycle can be initiated with the user interface 164, and the controller 162 can execute the stroke cycle, using the rotary position detected by the encoder 170 to determine when the guide wire 22 has reached an advanced or retracted state of the cycle.

In some examples, the control system 160 can include one or more alarms 174 for notifying a user about a particular circumstance. An alarm may correspond to, for example, a speaker that is operable to output a noise, or a diode that is operable to output a light. Each alarm 174 may be in communication with the controller 162, which can operate the alarm 174 to generate an output in response to a particular condition detected by the sensor(s) of the control system 160. For example, the controller 162 can operate an alarm 174 to generate an output if a torque detected in the first roller shaft 44 and/or second roller shaft 46 exceeds a predetermined threshold, or if a rotary position detected by the encoder 170 indicates that the spool 120 is improperly rotating (or not rotating). The control system can output various alarms, using various means, for indicating various circumstances detected by its sensor(s). For example, the control system may provide an alarm to a user via the user interface 164.

Additionally, the control system 160 can facilitate remote control and monitoring of the device 14. The control system 160 can be connected to a communication network, such as a wireless communication network, so that the device 14 can be monitored and/or controlled via a remote device, such as a computer or mobile device, e.g., a phone or tablet. Accordingly, any alarms 174 can be communicated over the network in order to send an alert to a device that may be in a remote or different location than the device 14. In addition to the alarms described above, data regarding usage and current or past states of the device 14 may be transmitted over the network. Data from various sensors in the device 14 can be collected in order to monitor the status and performance of the device 14. Examples of what can be monitored and/or controlled include: actuation cycles, drainage volume, location of clearance member, direction of movement of clearance member, pressure of system, battery power and status, alerts, alarms, errors, and fault codes. Also physiologic parameters such as drainage volumes and rates, air leak from lungs, $CO_2$ levels, ultrasound or echo data, drainage fluid parameters, hematocrit, activated clotting time, etc. can be monitored and/or controlled via the communication network. Moreover, the control system 160 can be configured to automatically change a status of the device 14 upon detecting a predetermined condition.

In some embodiments, the clearance device 14 can include a power supply 180 that can supply power to one or more of the features described above (e.g., the motor 102 and control system 160). The power supply 180 can include a battery holder 182, and one or more batteries 184 that can be inserted into the battery holder 182 to make electrical contact with battery terminals of the battery holder 182. However, the power supply 180 may include other means for supplying power such as, for example, a power cord that can be connected to an electrical outlet, or a receiver that can receive power wirelessly from a transmitter via an inductive coupling.

Figure 9:
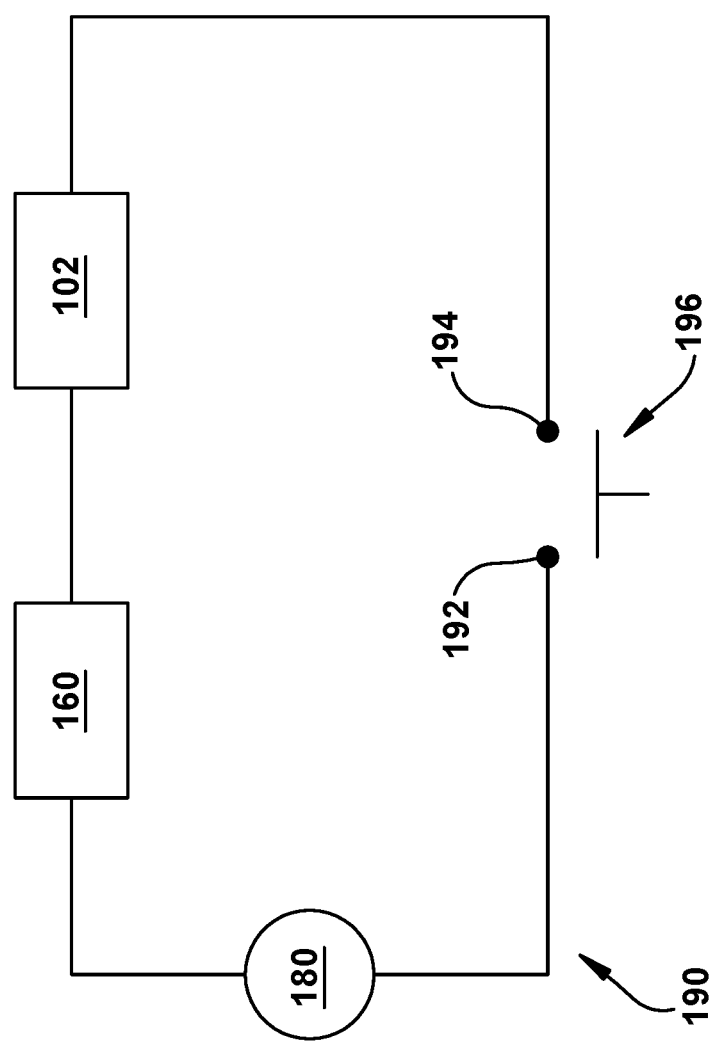
FIG. 9 is a schematic view of an example power circuit of the clearance device.

Turning to FIG. 9, the clearance device 14 can further include a power circuit 190 that can establish communication between the power supply 180 and the feature(s) requiring power. The power circuit 190 can include one or more wires, contacts, switches, or other circuit components for establishing communication along the power circuit 190. The power circuit 190 illustrated in FIG. 9 is schematic and configured to establish communication between the power supply 180, motor 102, and control system 160. However, it is to be appreciated that the power circuit 190 in FIG. 9 is merely an example, and may include alternative or additional paths and/or components in other examples.

In some examples, the power circuit 190 can be configured to enable selective communication between the power supply 180 and the powered feature(s). For example, the power circuit can include a first contact 192, a second contact 194, and a switch 196 that is movable relative to the first and second contacts 192, 194 to enable selective communication between the first and second contacts 192, 194 to selectively close the power circuit 190 between the first and second contacts 192, 194.

As shown in FIGS. 4 and 5, the first and second contacts 192, 194 of the power circuit 190 can be fixed within the housing 32. In particular, the first and second contacts 192, 194 can be fixed to the partition wall 54 located within the housing 32. Meanwhile, the carriage 60 described above can include a conductive portion 198 that corresponds to the switch 196 of the power circuit 190. The contacts 192, 194 and conductive portion 198 are arranged such that when the carriage 60 is in its disengaged position, the conductive portion 198 will be spaced from one or both contacts 192, 194 such that the power circuit 190 is open between the contacts 192, 194. Conversely, when the carriage 60 is in its engaged position, the conductive portion 198 will connect with and establish communication between both contacts 192, 194, thereby closing the power circuit 190 between the contacts 192, 194. In this manner, the power circuit 190 can be opened when the carriage 60 is in its disengaged position, in order to preserve battery life of the power supply 180 and/or prevent undesirable operation of the roller assembly 30 when disengaged from the guide wire 22. Further, when the spring 51 is a foam cylinder it may prevent accidental closure of the electronic circuit during use, transit, and storage of the device.

However, it is to be appreciated that the contacts 192, 194 and switch 196 of the power circuit 190 can be fixed to other features of the clearance device 14 without departing from the scope of the disclosure. For example, the contacts 192, 194 may be fixed to the carriage 60 and the switch 196 may correspond to a conductive portion of the wall 54 or some other feature of the device 14. Alternatively, the clearance device 14 may include a user-accessible power switch somewhere else along the housing 32, untethered to the carriage 60 or its operation.

As noted above, the housing 32 is designed to preserve a sterile field for the guide wire 22 and the roller assembly 30. In particular, as shown in FIGS. 2 and 3 the housing 32 defines an interior 34 wherein the guide wire 22 and rollers 48, 50 of the roller assembly 30 reside. The housing 32 forms a barrier between its interior 34 and exterior 36 so that the interior 34 can be sterilized and preserved in its sterilized state for the guide wire 22 and rollers 48, 50. Moreover, the housing 32 can contain one or more other features of the device 14 such as, for example, the motor 102, spool 120, power supply 180, and controller 162 described above.

A plurality of compartments can be defined within the housing 32 for the various features contained therein. For example, the housing 32 can define a roller compartment 202 that contains the first and second rollers 48, 50, a spool compartment 204 that contains the spool 120, and a motor compartment 206 that contains the motor 102 and controller 162.

Each compartment 202, 204, 206 can be defined by one or more walls of the device 14. For example, the roller compartment 202 can be defined by the shell halves 40, 42 of the housing 32, and the partition wall 54 of the roller assembly 30 when fixed within the housing 32. Moreover, the spool compartment 204 can be defined by one of the shell halves (e.g., shell half 40), the guide wall 134 described above, and a cover plate 210 fixed to the guide wall 134 that covers the spool compartment 204. Furthermore, the motor compartment 206 can correspond to the remaining space within the housing 32 that is defined by the shell halves 40, 42, the partition wall 54, the guide wall 134, and the cover plate 210. However, it is to be appreciated that each compartment 202, 204, 206 can be defined by other various walls of the housing 32 for the clearance device 14.

In examples wherein a plurality of compartments is defined within the housing 32, each compartment can be isolated from one or more other compartments such that fluid communication is inhibited therebetween, and that differential pressures are maintained therebetween. For example, the cover plate 210 can isolate the spool compartment 204 from the motor compartment 206, and a seal member 214 (e.g., gasket) can be provided along the guide wall 134 between the cover plate 210 and guide wall 134 to inhibit fluid communication between the guide wall 134 and cover plate 210. As another example, the partition wall 54 can separate the roller compartment 202 from the motor compartment 206. Moreover, a seal member 216 can be provided about the perimeter of the partition wall 54 to inhibit fluid communication between the partition wall 54 and the housing 32. Furthermore, another seal member 218 (see FIG. 5) can be provided about the first roller shaft 44 to inhibit fluid communication through the roller shaft opening 56 of the partition wall 54 separating the roller and motor compartments 202 and 206.

However, it is to be appreciated that each compartment can be isolated from one or more other compartments in a variety of different manners without departing from the scope of the disclosure. As each compartment can be isolated, it is to be appreciated that one or more compartments may remain sterile, while others do not remain sterile. Furthermore, some compartments may actually be in communication with each other. For example, the roller compartment 202 and spool compartment 204 can be in communication with each other through the guide conduit 144 described above.

As shown in FIG. 1, the clearance device 14 can be coupled to the medical tube 12 such that the guide wire 22 extends through the port 38 of the housing 32 and into the medical tube 12 through its proximal opening 18. Moreover, as discussed above, the clearance device 14 can be operated to advance and retract the guide wire 22 within the medical tube 12. In its fully retracted state, the guide wire 22 may be completely removed from the medical tube 12 and may reside completely within the housing 32 of the clearance device 14. Alternatively, the guide wire 22 may reside partially within the housing 32 and may extend partially into the medical tube 12. Meanwhile, in its fully advanced state, the guide wire 22 may extend through the medical tube 12 and out of its distal opening 16. Alternatively, the guide wire 22 may extend only partially through the medical tube 12 such that the guide wire 22 does not extend through its distal opening 16. It is to be appreciated that the guide wire 22 may assume a variety of different positions in its fully retracted and advanced states, the precise locations of which can be selected by the clinicians when configuring the clearance device 14 for a particular patient, pre-programmed by the manufacturer, or determined by physical stops, electrical sensors, or some combination thereof. Accordingly, it will be appreciated that a clinician or user can tune custom stroke lengths, as well as specify particular fully advanced and fully retracted positions for the guide wire 22 and any clearance member 24 attached thereto within the medical tube. Accordingly, the fully inserted position in a given, user- or pre-selected configuration need not be such that the distal end of the guide wire 22 or a clearance member 24 is received all the way adjacent to the distal end of the medical tube 12; and likewise the fully withdrawn position in a given, user- or pre-selected configuration need not be such that the distal end of that guide wire 22, or a clearance member 24, is located all the way adjacent to the proximal end of the medical tube 12, or withdrawn completely therefrom. Both fully inserted and fully withdrawn positions for a given stroke cycle can be defined at respective positions relative to the medical tube not corresponding to its distal and proximal ends.

In order to couple the clearance device 14 to the medical tube 12, the clearance device 14 can include a coupling portion 220 that defines its port 38. The coupling portion 220 can be defined by the housing 32 in a variety of configurations for directly or indirectly coupling to the medical tube 12. For example, the coupling portion 220 can have a frustoconical body that can be inserted directly into the proximal opening 18 of the medical tube 12. In another example, the coupling portion 220 can be indirectly coupled to the medical tube 12 via a connector 222, which is described in further detail below. At least one of the coupling portion 220 and the connector 222 includes a cleaning and/or lubricating element configured to wipe the guide wire 22 before it enters the device housing 32. For instance, the cleaning/lubricating element can be made from a foam material and configured to clear any blood residue from the guide wire 22. Additionally or alternatively, a reservoir can be coupled to the cleaning/lubricating element that includes at least one of a cleaning agent and/or a lubricating agent that is applied to the guide wire 22 during movement. The lubricant aids in reducing friction thereby reducing the required force to advance and retract the wire which in turn reduces power consumption. The cleaning/lubricating element can also be provided within the device housing 32.

Figure 10:
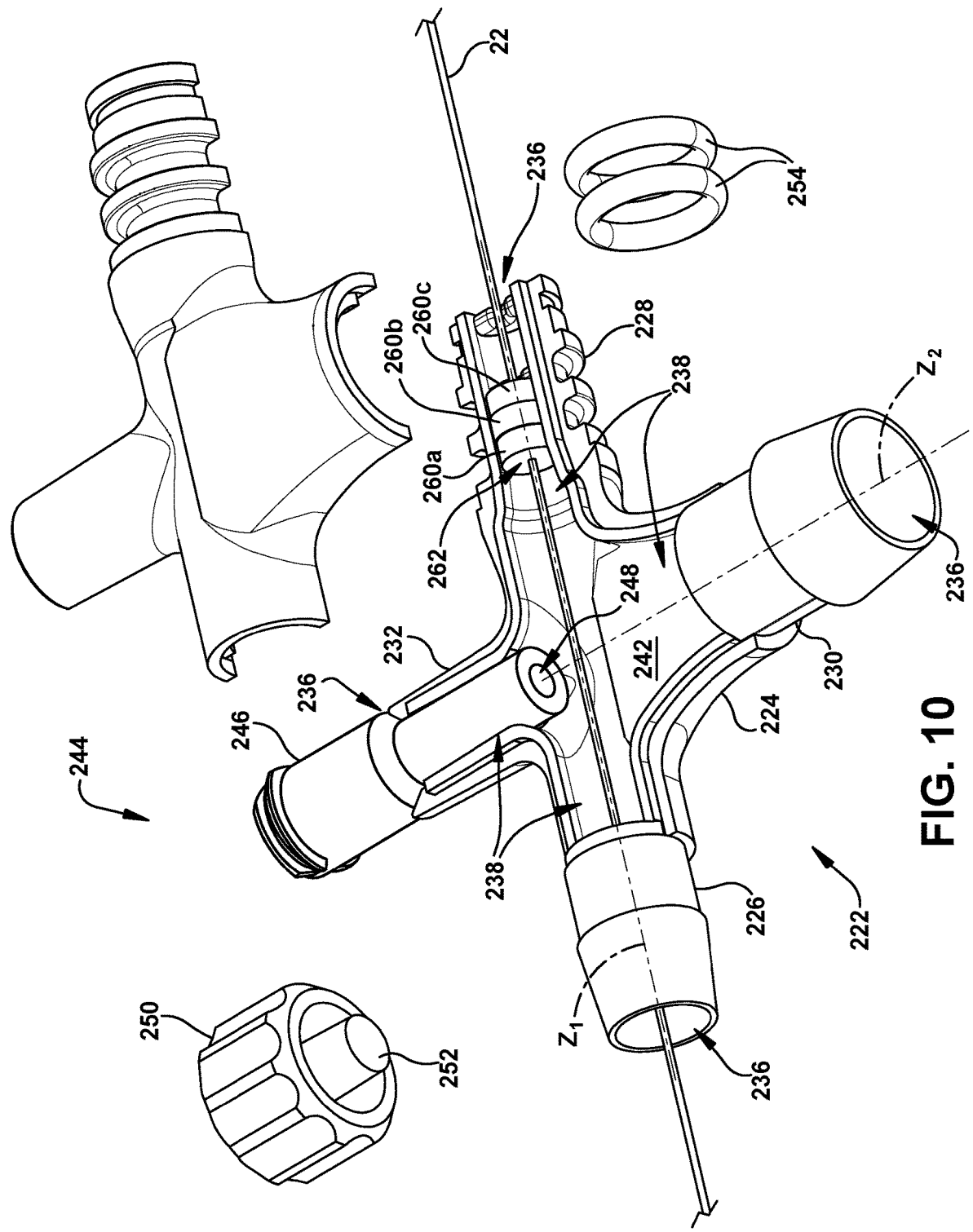
FIG. 10 shows a connector of the medical tube assembly with a housing portion thereof removed.

As shown in FIG. 10, the connector 222 includes a body 224 that defines multiple branches including a distal branch 226, a proximal branch 228, a drain branch 230, and an access branch 232. Each branch 226, 228, 230, 232 defines an opening 236 and a passageway 238 that extends into the body 224 from its opening 236. Moreover, the passageways 238 of the branches 226, 228, 230, 232 intersect at a hub chamber 242 within the body 224 such that the passageways 238 can communicate with each other via the hub chamber 242.

In the illustrated embodiment, the passageways 238 of the distal branch 226 and the proximal branch 228 are coaxial with a first connector axis $Z_1$, and the passageways 238 of the drain branch 230 and the access branch 232 are coaxial with a second connector axis $Z_2$ that is substantially perpendicular to and intersects the first connector axis $Z_1$. However, the first and second connector axes $Z_1$, $Z_2$ may be oblique to each other, and may not necessarily intersect with each other. Furthermore, one or both of the passageways 238 of the distal branch 226 and proximal branch 228 may be skewed relative to the first connector axis $Z_1$, and one or both of the passageways 238 of the drain branch 230 and access branch 232 may be skewed relative to the second connector axis $Z_2$. The passageways 238 can comprise a variety of different alignments without departing from the scope of the disclosure. Moreover, the number of passageways 238 can be varied as desired. For example, branch 232 may not be present in some configurations.

The distal branch 226 of the connector 222 can be directly coupled to the medical tube 12 such that the passageway 238 of the distal branch 226 is in fluid communication with the medical tube 12 via the opening 236 of the distal branch 226. Moreover, the proximal branch 228 can be directly coupled to the coupling portion 220 of the device 14 such that the passageway 238 of the proximal branch 228 is in fluid communication with the interior 34 of the device 14 via the opening 236 of the proximal branch 228. In this manner, the guide wire 22 can extend from the clearance device 14 through the passageways 238 of the distal and proximal branches 226, 228 of the connector 222 and into the medical tube 12. Moreover, because the passageways 238 of the distal and proximal branches 226, 228 are coaxial with a common, linear axis (i.e., first connector axis $Z_1$), the guide wire 22 can extend through the connector 222 along a linear path without having to navigate through any sharp bends or curves.

The drain branch 230, meanwhile, can be directly coupled to a drain tube 240 (see FIG. 1), which can drain fluids or other materials that are drawn into the connector 222 from the medical tube 12. In some examples, the drain tube 240 can be connected to a vacuum source, which will apply a vacuum to the drain tube 240 that facilitates the drawing of fluids or other materials from the medical tube 12 and through the connector 222 into the drain tube 240. In this manner, materials and fluids withdrawn from the medical tube 12 are withdrawn from the connector 222 via a pathway distinct from that leading to the clearance device 14, such that fouling and obstructing material is not drawn back into that device 14.

The access branch 232 can provide access to the interior of the connector 222 through its opening 236 and passageway 238. Such access may be achieved by intermittent or continuous connection through the access branch 232 and is desirable for clearing obstructions within the connector 222 and/or drain tube 240, delivering or removing fluids, gases, or other materials into the medical tube 12 or drain tube 240 through the access branch 232 and distal branch 226, or other various purposes. Clots, blood, gases, and/or other fluids can be withdrawn through the connector 222 for purposes of clearing an obstruction and/or sampling for testing. Additionally, in some examples, a cleaning fluid can be introduced into the connector 222 through the access branch 232 to dislodge obstructions in the connector 222. The fluid and obstructions can then be drained via the drain branch 230 and drain tube 240. In other examples, a pressure resulting from the injection or withdrawal of a fluid and/or gas into the connector 222 through the access branch 232 is used to clear obstructions from the medical tube 12 or the drain tube 240. That is, upon injecting a fluid the air and other gas within the drain branch and the medical tube becomes compressed behind any present obstruction. If a substantially incompressible liquid (e.g. water or aqueous solution) is injected, then the increased gas pressure will be due to the consumption by the injected liquid of available air space. Alternatively, if air or another gas (or combination of gases) is/are injected, then the increased gas pressure will be due to the addition of additional gaseous mass within the same volume behind the obstructing debris. In either case, the resulting additional pressure, itself or in combination with other features herein disclosed, can be useful to dislodge occluding debris within the medical tube 12. Conversely, withdrawal of fluid in front of (i.e. toward the proximal end of the tube 12) obstructing debris can yield a negative pressure in the associated tube space, which will tend to suck the obstructing debris out from the tube 12.

The connector 222 can include a valve assembly 244 that is operable to provide selective or continuous communication through the access branch 232. The valve assembly 244 can include a stem body 246 inserted into the passageway 238 of the access branch 232. The stem body 246 is a tubular body that defines a valve passage 248 extending through the stem body 246. Moreover, the stem body 246 is sized such that an outer diameter of the stem body 246 is substantially similar to the internal diameter of the access branch 232. In this manner, a seal can be established between the outer surface of the stem body 246 and the inner surface of the access branch 232. Meanwhile, the valve assembly 244 can further include a cap 250 that can be threadably connected to the stem body 246. The cap 250 includes a plug member 252 that will be inserted into the valve passage 248 of the stem body 246 when the cap 250 is completely threaded onto the stem body 246, thereby inhibiting fluid communication through the valve passage 248 and access branch 232. As the cap 250 is loosened from the stem body 246, the plug member 252 will be withdrawn from the valve passage 248 and fluid communication will be enabled through the valve passage 248 and access branch 232. The cap 250 can be completely removed from the stem body 246 to provide maximum communication through the valve passage 248 and access branch 232. However, it is to be appreciated that the valve assembly can be self-sealing without cap 250. Additionally, the access branch 232 and/or valve may be integral with the connector 222.

The valve assembly 244 described above can thus provide selective or continuous communication through the access branch 232, by loosening or tightening the threaded connection of its stem body 246 and cap 250. In this manner, the access branch 232 can be opened and closed as desired to provide selective access to the interior of the connector 222. However, it is to be appreciated that the connector 222 can include a variety of different valve assemblies for providing selective communication through the access branch 232. For example, the valve assembly 244 may be connected to a fluid or gas source in order to automatically introduce or remove materials (fluids, gas, solids, semi-solids) from the device 14 based on data from the various sensors in the device 14. The fluid or gas source may be a reservoir containing a sterile fluid or gas, filter atmospheric air, etc. If the sensors detect an obstruction in any of the tubes or pathways, the control system 16 can be configured to automatically introduce the fluid or gas from the fluid or gas source into the tube or pathway via the valve assembly 244. As noted above, the distal branch 226 of the connector 222 can be directly coupled to the medical tube 12, and the proximal branch 228 can be directly coupled to the coupling portion 220 of the clearance device 14. Moreover, the drain branch 230 can be directly coupled to a drain tube 240. Each of these branches 226, 228, 230 can have a variety of different configurations for directly coupling to their associated structures. For instance, each branch 226, 228, 230 can have a frustoconical body that can be inserted into its associated structure to couple the branch thereto.

Preferably, the proximal branch 228 of the connector 222 is configured to be rotatably coupled to the coupling portion 220 of the clearance device 14 such that the connector 222 is rotatable relative to the coupling portion 220 about the first connector axis $Z_1$. For example, the proximal branch 228 can be inserted into the coupling portion 220 of the clearance device 14, and one or more seals, such as O-rings 254, or any other suitable seal can be provided around the proximal branch 228 that establish a seal between the proximal branch 228 and the coupling portion 220 and permit the proximal branch 228 to rotate relative to the coupling portion 220 while maintaining their seal. This rotatable coupling of the connector 222 and coupling portion 220 can permit the connector 222 to be rotated relative to the clearance device 14 to accommodate different placements of that device 14, for example to ensure that the drain tube 240 has a downward orientation for gravity purposes.

However, it is to be appreciated that the proximal branch 228 of the connector 222 can be rotatably coupled to the coupling portion 220 of the clearance device 14 in a variety of different ways without departing from the scope of this disclosure. Furthermore, one or both of the distal branch 226 and drain branch 226 of the connector 222 may be similarly rotatably coupled to the medical tube 12 and drain tube 240.

The connector 222 can include one or more guide bodies 260 within its proximal branch 228 to center the guide wire 22 through the connector 222. Each guide body 260 can be tubular in shape, with an outer diameter that closely approximates the inner diameter of the proximal branch 228, and a through-hole 262 that is coaxial with the first connector axis $Z_1$. The diameter of the through-hole 262 can closely approximate the diameter of the guide wire 22, although the diameter may be larger such that a small clearance is provided between the guide wire 22 and guide body 260. Alternatively, the diameter of the through-hole 262 can be smaller than the guide wire 22 in order to create an interference fit with the guide wire 22.

In the illustrated embodiment, the connector 222 includes three guide bodies 260 (260a, 260b, and 260c) arranged within its proximal branch 228 that are aligned along the first connector axis $Z_1$. The middle guide body 260b is made of thermoplastic polyurethane or some other material such as, silicone, other types of rubber, thermoplastic elastomers, etc. that can establish a seal between the guide wire 22 and proximal branch 228. The middle guide body 260b acts as a septum forming a seal with the guide wire 22 as it translates that can preserve a vacuum within the connector 222 from the drain tube 240. Meanwhile, the outer guide bodies 260a, 260c can be made of Teflon or some other material such as PEEK, acetal plastic, etc. that can minimize friction between the guide bodies 260 and guide wire 22 passing through. The guide bodies 260 act to seal and separate the housing 32 from a blood path. In addition, when the guide wire 22 passes through the guide bodies 260, the internal diameter of the guide bodies 260 are configured to wipe the guide wire 22 clean to limit travel of blood or other material carried by the guide wire 22 into the device housing 32.

The number and arrangement of guide bodies 260 may vary in other examples, as well as the materials of the guide bodies 260. A seal is provided between an outer portion of the guide bodies 260 and the connector 222, to restrict fluid flow around and between the guide bodies 260. This seals assists in the maintenance of a vacuum in the tube system, mitigates the ingress of fluids into the enclosure, and maintains sterility of the medical tube circuit. The seals can be achieved by positioning a seal member between one or more of the guide bodies 260 and the connector 222. The seal member can be RTV silicone, O-rings, or other means that are integral or coupled to at least one of the guide bod(ies) 260 or the connector 222.

The clearance device 14 described above can be a modular, self-contained unit including all of the foregoing features. In the illustrated embodiments, the modular clearance device 14 is a portable device that can be placed on a patient's body, for example, preferably close to where the medical tube 12 exits the body. To ensure that the device 14 remains properly seated on the patient's body, the device 14 can include a substrate 264 (see FIG. 11) having adhesive, e.g. an acrylic adhesive designed for skin contact or a hydrocolloid type material, on its exposed surface that can be adhered to the patient's body. The substrate 264 preferably is made from foam or some other flexible material that can flex to accommodate variable, curved or irregular profiles of the patient's body while remaining adhered to the housing 32 at its opposite surface. In another embodiment, the adhesive pad may have a carrier or other features that allow securement and detachment of the device 14 to and from the patient without removing and reapplying the adhesive pad. The carrier may be plastic and allow snap connection or could have other fastening mechanisms, such as a hook and loop fasteners. Alternatively, the device 14 may be secured to the patient via a strap, such as a belt strap, or as part of a garment, such as a vest that can secure the device within pockets, loops, or other features. Or, the device 14 may not be coupled to the patient at all. The device 14 can be secured to other devices or equipment, such as walkers, beds, IV poles, etc. through similar fastening mechanisms discussed above.

Figure 11:
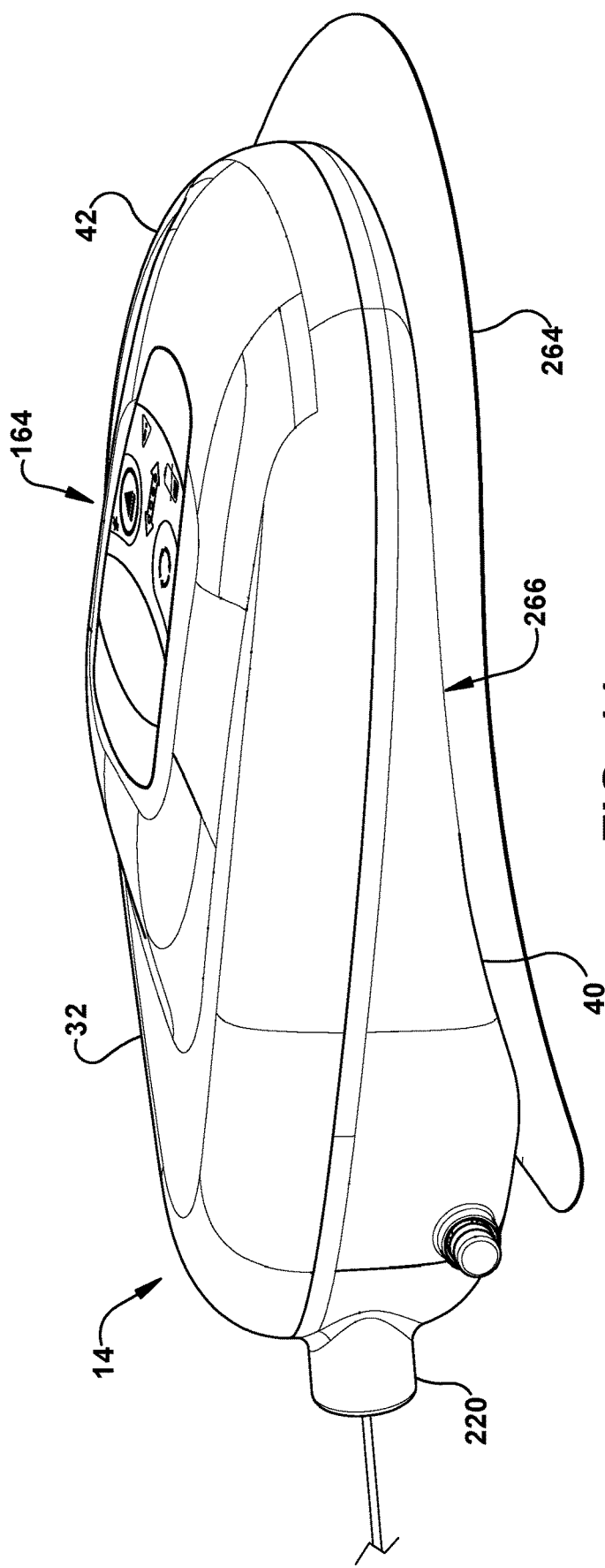
FIG. 11 is a side-perspective view of the clearance device and a flexible substrate adhered to the clearance device.

As further shown in FIG. 11, the housing 32 can have a contour designed to conform better to a patient's body (as compared to, for example, a flat profile). More specifically, the housing 32 can define a lower surface 266 that is intended to face and rest on the patient's body. The lower surface 266 can be concave so as to more naturally accommodate the curvature of a patient's body (for example the patient's leg or abdomen) against or to which it rests or is adhered in practice. One side of the substrate 264 described above can be adhered to this lower surface 266, while the opposite side of the substrate 264 is available for adhesion to the patient's body, e.g. via medical-grade adhesive. In this manner, the housing 32 can be conveniently fixed, temporarily, to and against the patient's body.

The modular clearance device 14, including the controller 162, user interface 164, roller assembly 30, and spool 120 can be configured so that the device 14 is reusable between different patients. For example, the foam substrate 264 may be removable and discarded as a consumable item, and the clearance device 14 itself, including its housing 32 and all interior components, can be reprocessed for subsequent use with additional patients. Accordingly, the device 14 can be a modular, portable device usable successively for different patients, and can be conveniently stored and transported to different treatment sites or rooms within a hospital or other clinical setting. In such examples, the actuator 64 described above can be released from its locked state and returned to its second position after use with a patient, in order to return the carriage 60 to its disengaged position and enable fluid communication through the guide channel 80 for a sterilizing fluid to be introduced and/or evacuated into and/or from the housing 32. In some embodiments, for single use or multi-use, the device 14 can have one or more battery compartments in which replaceable batteries can be accessed without compromising the sterile barrier or vacuum seal. Additionally or alternatively, the device 14 may include a mechanism for recharging internal batteries either through direct electrical connection or inductive charging.

Alternatively, the device 14 may be disposable so that after the device 14 is used with a patient, the device 14 may be discarded. Indeed, in such embodiments, the device 14 can include one or more locking features (e.g., the catch 92 described above) that prohibit the actuator 64 from returning to its second position, thus preventing a technician from re-establishing fluid communication through the guide channel 80 for a sterilizing fluid.

Illustrative embodiments have been described, hereinabove. It will be apparent to those skilled in the art that various modifications and variations can be made without departing from the spirit and scope of the claimed invention. It is intended to include all such modifications and alterations within the scope of the present invention.

What is claimed is:

1. A device for clearing obstructions from a medical tube, comprising:
   a housing defining an interior, an exterior, and a port providing communication therebetween;
   an elongated guide wire residing at least partially within the housing;
   first and second rollers adapted to define a nip therebetween;
   a motor within said housing operable to drive at least one of the first roller and the second roller in order to drive said guide wire through said nip; and
   a user interface on said housing accessible from said exterior;
   said guide wire adapted to extend through said nip and be drivable for advancement and retraction thereof through said port via rotation of said rollers;
   said device being a self-contained, portable unit.

2. The device according to claim 1, further comprising:
   a first roller shaft, said first roller being coupled to the first roller shaft and rotatable therewith about a first roller axis,
   a second roller shaft, said second roller being coupled to the second roller shaft and rotatable therewith about a second roller axis, and a transmission operatively connected to each of said first and second roller shafts and configured to synchronize rotation thereof about their associated roller axes in opposing directions.

3. The device according to claim 2, the transmission comprising a first gear fixed to the first roller shaft and a second gear fixed to the second roller shaft.

4. The device according to claim 1, further comprising:
   a wall that defines a roller shaft opening, a first roller shaft extending through the roller shaft opening, and
   a seal member provided about the first roller shaft that inhibits fluid communication through the roller shaft opening.

5. The device according to claim 1, the second roller being rotatably supported by a movable carriage configured to move between a disengaged position where said second roller does not interact with the first roller and an engaged position where said second roller interacts with said first roller to thereby define said nip therebetween.

6. The device according to claim 5, the carriage being pivotable about a carriage axis that is spaced from and substantially parallel to a second roller axis in order to move said carriage between said disengaged and engaged positions.

7. The device according to claim 5, further comprising a power circuit for supplying electrical energy to a motor for rotating at least one of said first and second rollers, said carriage being configured to open the power circuit when said carriage is in the disengaged position and to close said power circuit when said carriage is in the engaged position.

8. The device according to claim 5, further comprising an actuator that is accessible from said exterior to move the actuator from a first position to a second position, the actuator being configured to move the carriage from the disengaged position to the engaged position as the actuator is moved from the first position to the second position.

9. The device according to claim 8, wherein the actuator includes a cam body with a cam surface that engages the carriage as the actuator is moved from the first position to the second position to move the carriage from the disengaged position to the engaged position.

10. The device according to claim 8, further comprising:
a guide passage having an inner surface, the actuator being slidably received through the guide passage, and
a seal member configured to establish a seal between the actuator and the inner surface of the guide passage.

11. The device according to claim 10, wherein:
when the actuator is in the first position, the interior and exterior of the housing are in fluid communication through the guide passage, and
when the actuator is in the second portion, said seal inhibits fluid communication through the guide passage.

12. The device according to claim 1, further comprising a spool within the housing for dispensing and accumulating the elongated guide wire, the spool being rotatable relative to the housing about a spool axis.

13. The device according to claim 12, wherein:
the elongated guide wire is coupled to the spool, and
the spool is configured to freely rotate relative to the housing such that the spool passively rotates in response to compressive and tensile forces in the elongated guide wire as the elongated guide wire is driven through the nip.

14. The device according to claim 12, further comprising a guide wall that extends at least partially about the circumference of the spool, the guide wall having an axis of curvature that is coaxial with the spool axis.

15. The device according to claim 14, wherein the guide wall comprises a rim and a plurality of guide projections that extend radially inward from the rim toward the spool and are circumferentially spaced about the spool.

16. The device according to claim 12, further comprising:
a magnet coupled to the spool, and
an encoder configured to detect a rotary position of the magnet about the spool axis.

17. The device according to claim 12, further comprising a shelf of the housing that includes a plurality of recesses.

18. The device according to claim 17, wherein the plurality of recesses are configured to collect debris introduced into the housing via the guide wire.

19. The device according to claim 17, wherein the plurality of recesses reduce surface contact between the guide wire and the shelf.

20. The device according to claim 1, an outer surface portion of said housing being concave in order to accommodate a curvature of a patient's body to which said device is to be mounted in use.

21. The device according to claim 20, further comprising a flexible substrate adhered and conforming to said concave outer surface portion and having an exposed surface with an adhesive for adhering said device to the patient's body in use.

22. The device according to claim 1, further comprising:
a power supply within said housing coupled to said motor via a power circuit to supply electrical energy thereto; and
a controller within said housing operatively coupled to said motor and to said user interface, and configured to receive user inputs from said user interface for directing the advancement or withdrawal of said guide wire, and to control operation of said motor for driving said guide wire based on said user inputs.

23. The device according to claim 1, the first and second rollers located within said housing.

24. A medical tube assembly comprising the device according to claim 1, the medical tube, and a connector for connecting the device to the medical tube, wherein:
the connector comprises a body that defines a distal branch, a proximal branch, and a drain branch, all of which being in fluid communication with one another via a common hub chamber, and
the proximal branch is rotatably coupled to said port in order to accommodate said guide wire therethrough.

25. The medical tube assembly according to claim 24, wherein the connector comprises one or more guide bodies within the proximal branch, each guide body being tubular in shape with an outer diameter that approximates an inner diameter of the proximal branch, and a through-hole that extends through each of the guide bodies.

26. The medical tube assembly according to claim 24, wherein:
the body of the connector further defines an access branch in fluid communication with the hub chamber, and
the connector further includes a valve assembly that is operable to provide selective communication through the access branch.

27. A device for clearing obstructions from a medical tube, comprising:
a housing defining an interior, an exterior, and a port providing fluid communication therebetween;
an elongated guide wire residing at least partially within the housing;
first and second rollers adapted to define a nip therebetween;
a motor within said housing operable to drive at least one of the first roller and the second roller in order to drive said guide wire through said nip; and
a user interface on said housing accessible from said exterior;
an outer surface portion of the housing is concave in order to accommodate a curvature of a patient's body to which the device is to be mounted in use;
said guide wire is adapted to be drivable for advancement and retraction through said port and into a medical tube.

* * * * *

UNITED STATES PATENT AND TRADEMARK OFFICE
CERTIFICATE OF CORRECTION

PATENT NO. : 10,881,484 B2
APPLICATION NO. : 16/740988
DATED : January 5, 2021
INVENTOR(S) : Edward M. Boyle, Jr. et al.

Page 1 of 1

It is certified that error appears in the above-identified patent and that said Letters Patent is hereby corrected as shown below:

In the Claims

In Claim 11, at Column 25, Line 19, please delete "second portion" and replace it with -- second position --

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*